(12) United States Patent
Kim

(10) Patent No.: US 11,666,479 B2
(45) Date of Patent: Jun. 6, 2023

(54) DEVICE FOR COOLING ANESTHESIA BY CHILLED FLUIDIC COOLING MEDIUM

(71) Applicant: RECENSMEDICAL, INC., Ulsan (KR)

(72) Inventor: Gun-Ho Kim, Ulsan (KR)

(73) Assignee: RECENSMEDICAL, INC., Ulsan (KR)

( * ) Notice: Subject to any disclaimer, the term of this patent is extended or adjusted under 35 U.S.C. 154(b) by 961 days.

(21) Appl. No.: 16/544,539

(22) Filed: Aug. 19, 2019

(65) Prior Publication Data

US 2020/0054483 A1 Feb. 20, 2020

Related U.S. Application Data

(60) Provisional application No. 62/756,018, filed on Nov. 5, 2018, provisional application No. 62/719,695, filed on Aug. 19, 2018.

(51) Int. Cl.
*A61F 7/00* (2006.01)
*A61M 11/00* (2006.01)

(52) U.S. Cl.
CPC ......... *A61F 7/0085* (2013.01); *A61M 11/005* (2013.01); *A61F 2007/0004* (2013.01); *A61F 2007/0063* (2013.01); *A61F 2007/0076* (2013.01); *A61M 2209/088* (2013.01)

(58) Field of Classification Search
CPC ...................................... A61F 9/068
See application file for complete search history.

(56) References Cited

U.S. PATENT DOCUMENTS

| 2,044,823 | A | 6/1936 | Whiteside |
| 4,646,735 | A | 3/1987 | Seney |
| 6,099,521 | A | 8/2000 | Shadduck |
| 6,141,985 | A | 11/2000 | Cluzeau et al. |

(Continued)

FOREIGN PATENT DOCUMENTS

| CN | 2660834 Y | 12/2004 |
| EP | 1 030 611 B1 | 9/2004 |

(Continued)

OTHER PUBLICATIONS

Chinese First Office Action dated Dec. 22, 2020 for CN 201780083128.0.

(Continued)

*Primary Examiner* — Kaitlyn E Smith
(74) *Attorney, Agent, or Firm* — Knobbe, Martens, Olson & Bear, LLP

(57) ABSTRACT

A hand-held or wearable device for cooling tissue of an eye of a patient is disclosed. In one aspect, the device includes a reservoir having fluid therein and a support connected to the reservoir and configured to be positioned on a face of the patient. The device also includes a nozzle positioned proximate to the support and fluidically connected to the reservoir, the nozzle configured to pass the fluid from the reservoir onto a surface of the eye. The device further includes a cooling element configured to cool the fluid from the reservoir such that it exits the nozzle at a temperature of between −100° C. and 15° C. The device further includes an ultrasonic vibrator positioned near the nozzle and configured to generate mist from at least part of the fluid.

18 Claims, 28 Drawing Sheets

(56) References Cited

U.S. PATENT DOCUMENTS

| | | |
|---|---|---|
| 6,632,219 B1 | 10/2003 | Baranov et al. |
| 6,669,688 B2 | 12/2003 | Svaasand et al. |
| 7,037,326 B2 | 5/2006 | Lee |
| 7,780,656 B2 | 8/2010 | Tankovich |
| 7,963,959 B2 | 6/2011 | Silva et al. |
| 8,083,734 B2 | 12/2011 | Steinfatt et al. |
| D658,775 S | 5/2012 | Jiangminhui |
| 8,177,827 B2 | 5/2012 | Shapiro |
| 8,256,233 B2 | 9/2012 | Boyden et al. |
| 8,409,184 B2 | 4/2013 | Baust et al. |
| 8,652,131 B2 | 2/2014 | Muller et al. |
| 8,672,879 B2 | 3/2014 | Grant et al. |
| 8,747,397 B2 | 6/2014 | Baust et al. |
| 8,788,060 B2 | 7/2014 | Nebrigic et al. |
| 8,858,583 B2 | 10/2014 | Shtram et al. |
| 9,017,318 B2 | 4/2015 | Fourkas et al. |
| 9,039,688 B2 | 5/2015 | Palmer, III et al. |
| 9,066,712 B2 | 6/2015 | Fourkas et al. |
| 9,113,855 B2 | 8/2015 | Burger et al. |
| 9,155,584 B2 | 10/2015 | Fourkas et al. |
| 9,398,975 B2 | 7/2016 | Müller et al. |
| 9,522,031 B2 | 12/2016 | Anderson et al. |
| 9,549,773 B2 | 1/2017 | Anderson et al. |
| 9,642,741 B2 | 5/2017 | Feng et al. |
| 9,801,677 B2 | 10/2017 | Anderson et al. |
| 9,855,166 B2 | 1/2018 | Anderson et al. |
| 9,956,355 B2 | 5/2018 | Besirli et al. |
| 9,974,684 B2 | 5/2018 | Anderson et al. |
| D822,841 S | 7/2018 | Cheng |
| 10,085,881 B2 | 10/2018 | Karnik et al. |
| 10,154,870 B2 | 12/2018 | Ottanelli |
| 10,188,444 B2 | 1/2019 | Fourkas et al. |
| 10,213,244 B2 | 2/2019 | Fourkas et al. |
| 10,322,248 B2 | 6/2019 | Besirli et al. |
| 10,349,997 B1 | 7/2019 | O'Reilly |
| 10,363,080 B2 | 7/2019 | Elkins et al. |
| 10,543,032 B2 | 1/2020 | Babkin |
| 2004/0102768 A1 | 5/2004 | Cluzeau et al. |
| 2004/0111087 A1 | 6/2004 | Stern et al. |
| 2005/0005626 A1 | 1/2005 | McMahon |
| 2005/0059940 A1 | 3/2005 | Weber et al. |
| 2005/0261753 A1 | 11/2005 | Littrup et al. |
| 2006/0200117 A1 | 9/2006 | Hermans |
| 2006/0213509 A1 | 9/2006 | Marin et al. |
| 2007/0005048 A1 | 1/2007 | Niedbala et al. |
| 2008/0164296 A1 | 7/2008 | Shelton et al. |
| 2008/0221561 A1 | 9/2008 | Geiger et al. |
| 2009/0036846 A1 | 2/2009 | Dacquay et al. |
| 2009/0062751 A1 | 3/2009 | Newman, Jr. |
| 2009/0124972 A1 | 5/2009 | Fischer et al. |
| 2009/0149930 A1 | 6/2009 | Schenck |
| 2009/0163902 A1 | 6/2009 | DeLonzor et al. |
| 2010/0010480 A1 | 1/2010 | Mehta et al. |
| 2010/0087805 A1 | 4/2010 | Citterio et al. |
| 2010/0196343 A1 | 8/2010 | O'Neil et al. |
| 2010/0198207 A1 | 8/2010 | Elkins et al. |
| 2011/0072834 A1 | 3/2011 | Ishikura et al. |
| 2011/0098791 A1 | 4/2011 | Kim |
| 2011/0137268 A1 | 6/2011 | Thomason et al. |
| 2011/0152850 A1 | 6/2011 | Niedbala et al. |
| 2011/0177474 A1 | 7/2011 | Jamnia et al. |
| 2011/0224761 A1 | 9/2011 | Manstein |
| 2012/0130458 A1 | 5/2012 | Ryba et al. |
| 2012/0191166 A1 | 7/2012 | Callister et al. |
| 2012/0232549 A1 | 9/2012 | Willyard et al. |
| 2012/0265278 A1 | 10/2012 | Fourkas et al. |
| 2013/0116719 A1 | 5/2013 | Shtram et al. |
| 2013/0184694 A1 | 7/2013 | Fourkas et al. |
| 2013/0296811 A1 | 11/2013 | Bangera et al. |
| 2013/0315924 A1 | 11/2013 | Hsu et al. |
| 2014/0012226 A1 | 1/2014 | Hochman |
| 2014/0187969 A1* | 7/2014 | Hunter ............ A61B 5/4839 604/521 |
| 2014/0200511 A1 | 7/2014 | Boyden et al. |
| 2014/0277023 A1 | 9/2014 | Sekino et al. |
| 2014/0303608 A1 | 10/2014 | Taghizadeh |
| 2015/0018781 A1* | 1/2015 | Rinderknect ......... A61F 9/0026 604/298 |
| 2015/0051545 A1 | 2/2015 | Henderson et al. |
| 2016/0058488 A1 | 3/2016 | Fourkas et al. |
| 2016/0135864 A1 | 5/2016 | Babkin |
| 2016/0143802 A1 | 5/2016 | Tranfaglia et al. |
| 2016/0183996 A1 | 6/2016 | Burger et al. |
| 2016/0242956 A1 | 8/2016 | Gomez |
| 2016/0262820 A1 | 9/2016 | Allison et al. |
| 2016/0279350 A1* | 9/2016 | Besirli .................. A61M 5/315 |
| 2017/0014174 A1 | 1/2017 | Levine et al. |
| 2017/0062793 A1 | 3/2017 | Zakharyan et al. |
| 2017/0231816 A1 | 8/2017 | Ryan |
| 2017/0232243 A1 | 8/2017 | Herweijer |
| 2017/0304558 A1 | 10/2017 | Besirli et al. |
| 2017/0354451 A1 | 12/2017 | Marin et al. |
| 2018/0116705 A1 | 5/2018 | Lee et al. |
| 2018/0235805 A1 | 8/2018 | Burger et al. |
| 2018/0310979 A1 | 11/2018 | Peled et al. |
| 2019/0000524 A1 | 1/2019 | Rosen et al. |
| 2019/0015146 A1 | 1/2019 | DuBois et al. |
| 2019/0038459 A1 | 2/2019 | Karnik et al. |
| 2019/0175394 A1 | 6/2019 | Kim |
| 2019/0175395 A1 | 6/2019 | Kim |
| 2019/0175396 A1 | 6/2019 | Kim |
| 2019/0239938 A1 | 8/2019 | Kazic et al. |
| 2019/0254866 A1 | 8/2019 | Whiteley et al. |
| 2019/0290881 A1 | 9/2019 | Kim |
| 2020/0007882 A1 | 1/2020 | Abe et al. |
| 2020/0007883 A1 | 1/2020 | Toresson |
| 2020/0100934 A1 | 4/2020 | Ariano et al. |
| 2020/0309436 A1 | 10/2020 | Kim |

FOREIGN PATENT DOCUMENTS

| | | |
|---|---|---|
| EP | 1 401 347 B1 | 8/2011 |
| EP | 2 010 087 B1 | 11/2014 |
| EP | 2 910 276 A1 | 8/2015 |
| EP | 2 759 272 B1 | 11/2018 |
| JP | 04-092663 A | 3/1992 |
| JP | 06-086818 A | 3/1994 |
| JP | 10-230435 A | 9/1998 |
| JP | 2002-505155 A | 2/2002 |
| JP | 4049358 B2 | 2/2002 |
| JP | 2004-515270 A | 5/2004 |
| JP | 2005-080832 A | 3/2005 |
| JP | 2008-212638 A | 9/2008 |
| JP | 2008-545462 A | 12/2008 |
| JP | 2009-034273 A | 2/2009 |
| JP | 2009-056320 A | 3/2009 |
| JP | 2011-077314 A | 4/2011 |
| JP | 2012-143279 A | 8/2012 |
| JP | 2013-142410 A | 7/2013 |
| JP | 2014-198238 A | 10/2014 |
| JP | 2015-510802 A | 4/2015 |
| JP | 2017-113635 A | 6/2017 |
| KR | 20-1998-0005117 U | 3/1998 |
| KR | 2019-980005117 U | 3/1998 |
| KR | 10-0200669 B1 | 3/1999 |
| KR | 10-2003-0068633 A | 8/2003 |
| KR | 10-2004-0093706 A | 11/2004 |
| KR | 10-0786539 B1 | 12/2007 |
| KR | 10-0790758 B1 | 12/2007 |
| KR | 10-2008-0045022 A | 5/2008 |
| KR | 10-0851274 B1 | 8/2008 |
| KR | 10-2010-0041207 A | 4/2010 |
| KR | 10-2010-0060222 A | 6/2010 |
| KR | 10-2010-0135863 A | 12/2010 |
| KR | 10-1053835 B1 | 8/2011 |
| KR | 10-2011-0119640 A | 11/2011 |
| KR | 10-2012-0115703 A | 10/2012 |
| KR | 10-2013-0087770 A | 8/2013 |
| KR | 10-1366126 B1 | 2/2014 |
| KR | 10-1386137 B1 | 4/2014 |
| KR | 10-2014-0052667 A | 5/2014 |
| KR | 10-2014-0069431 A | 6/2014 |
| KR | 10-2015-0030264 A | 3/2015 |
| KR | 10-2015-0062492 A | 6/2015 |

(56) References Cited

FOREIGN PATENT DOCUMENTS

| KR | 10-2016-0048425 A | 5/2016 |
|---|---|---|
| KR | 10-2016-0146337 A | 12/2016 |
| KR | 10-1707659 B1 | 2/2017 |
| KR | 10-1719459 B1 | 3/2017 |
| KR | 10-2017-0041776 A | 4/2017 |
| KR | 10-2017-0083399 A | 7/2017 |
| KR | 10-2017-0089842 A | 8/2017 |
| KR | 10-1813652 B1 | 8/2017 |
| KR | 10-2017-0130470 A | 11/2017 |
| KR | 10-1819204 B1 | 1/2018 |
| KR | 10-2018-0054247 A | 5/2018 |
| KR | 10-1840346 B1 | 5/2018 |
| KR | 10-1862127 B1 | 5/2018 |
| KR | 10-2018-0109828 A | 10/2018 |
| KR | 10-1936890 B1 | 1/2019 |
| KR | 10-2019-0074150 A | 6/2019 |
| WO | WO 2016/154399 A1 | 9/2016 |
| WO | WO 2018/231868 A1 | 12/2018 |

OTHER PUBLICATIONS

European (EUIPO) Examination Report dated Jan. 11, 2021 for 008309504-003.
European (EUIPO) Examination Report dated Feb. 5, 2021 for 008309504-003.
International Search Report dated Mar. 4, 2021, for PCT/KR2020/012886.
International Written Opinion dated Mar. 4, 2021, for PCT/KR2020/012886.
Office Action dated Sep. 13, 2019 for U.S. Appl. No. 16/412,296.
Final Office Action dated Jan. 31, 2020 for U.S. Appl. No. 16/412,296.
Final Office Action dated Oct. 28, 2020 for U.S. Appl. No. 16/412,296.
Office Action Dated Dec. 24, 2020 for U.S. Appl. No. 17/036,269.
Office Action dated Dec. 8, 2020 for U.S. Appl. No. 17/036,311.
Notice of Allowance dated Feb. 22, 2021 for U.S. Appl. No. 17/036,311.
Office Action dated Nov. 5, 2020 for U.S. Appl. No. 29/701,630.
Notice of Allowance dated Feb. 3, 2021 for U.S. Appl. No. 29/701,630.
Office Action dated Nov. 5, 2020 for U.S. Appl. No. 29/701,631.
Notice of Allowance dated Feb. 3, 2021 for U.S. Appl. No. 29/701,631.
Korean Office Action dated Nov. 26, 2019 for KR 10-2018-0049108.
Korean Office Action dated Nov. 27, 2019 for KR 10-2018-0049109.
Korean Office Action dated Dec. 6, 2019 for KR 10-2018-0049110.
Korean Office Action dated Dec. 9, 2019 for KR 10-2018-0049115.
Korean Office Action dated Dec. 10, 2019 for KR 10-2018-0049117.
International Search Report dated Jun. 4, 2018 for PCT/KR2017/012935.
International Search Report dated Jul. 6, 2018 for PCT/KR2018/003773.
International Search Report dated Aug. 8, 2018 for PCT/KR2017/013901.
International Search Report dated May 30, 2019 for PCT/KR2018/016491.
Korean Notice of Allowance dated Jun. 30, 2018 for KR 10-2016-0151947.
Korean Office Action dated Oct. 22, 2018 for KR 10-2017-0162715.
Korean Office Action dated Oct. 22, 2018 for KR 10-2017-0162716.
Korean Office Action dated Jul. 29, 2019 for KR 10-2017-0162717.
Korean Notice of Allowance dated Jul. 29, 2019 for KR 10-2017-0162716.
Korean Notice of Allowance dated Aug. 29, 2019 for KR 10-2017-0162715.
Korean Office Action dated Oct. 8, 2019 for KR 10-2018-0052601—no translation avail.
International Search Report and Written Opinion dated Aug. 14, 2019 for PCT/KR2019/005105.
International Search Report and Wrillen Opinion dated Nov. 15, 2019 for PCT/KR2019/009411.
Korean Final Office Action dated Jan. 17, 2020 for KR 10-2017-0162717 with Translation.
Korean Final Office Action dated May 10, 2020, for KR 10-2018-0049109 with Translation.
Korean Notice of Allowance dated Jun. 24, 2020 for KR 10-2018-0049109—w/ Trans.
Korean Final Office Action dated May 10, 2020 for KR 10-2018-0049110—w/ Trans.
Korean Notice of Allowance dated Jun. 22, 2020 for KR 10-2018-0049110—w/ Trans.
Korean Notice of Allowance dated Jul. 21, 2020 for KR 10-2018-0049115—w/ Trans.
Korean Notice of Allowance dated May 10, 2020 for KR 10-2018-0049117.
Korean Second Office Action, with translation, dated Oct. 28, 2019 for KR 10-2018-0052601.
Korean Office Action dated Oct. 22, 2018, for KR 10-2018-0117138.
Smith et al., "Ice Anesthesia for Injection of Dermal Fillers," The American Society for Dermatologic Surgery Inc., Dermatol. Surg 2010;36:812-814, 2010.
Sarifakiogiu, et al., "Evaluating the Effects of Ice Application on the Pain Feit During Botulinum Toxin Type-A Injections," Annals of Plastic Surgery, vol. 53, No. 6, Dec. 2004.
International Search Report dated Mar. 27, 2020, for PCT/KR2019/017328.
Korean Notice of Allowance dated Apr. 2, 2020 for KR 10-2018-0052601 with Eng. Translation.
Korean Office Action dated May 10, 2020 for KR10-2018-0049115, with Eng. Translation.
Office Action dated Oct. 2, 2019 for U.S. Appl. No. 15/828,449.
Office Action dated May 15, 2020 for U.S. Appl. No. 15/828,449.
Office Action dated Jun. 26, 2020 for U.S. Appl. No. 16/412,296.

* cited by examiner

221

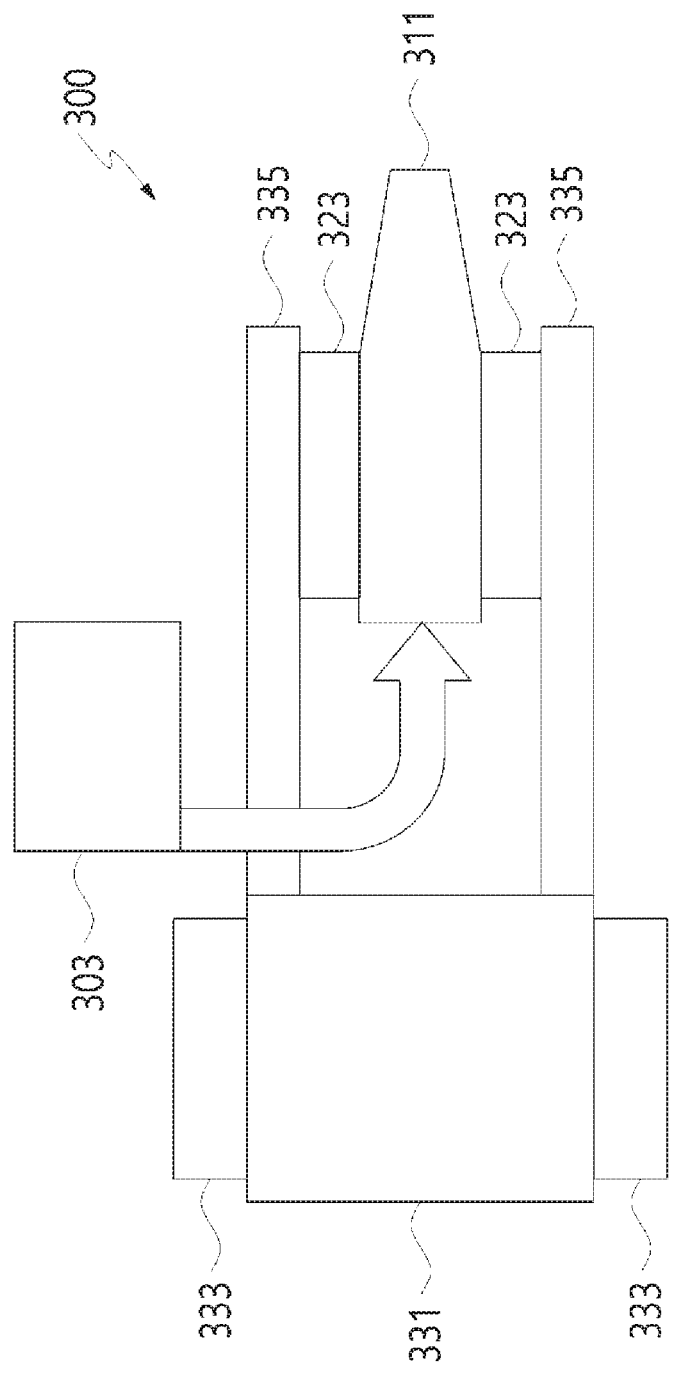

⊘ : nozzle

FIG. 7C
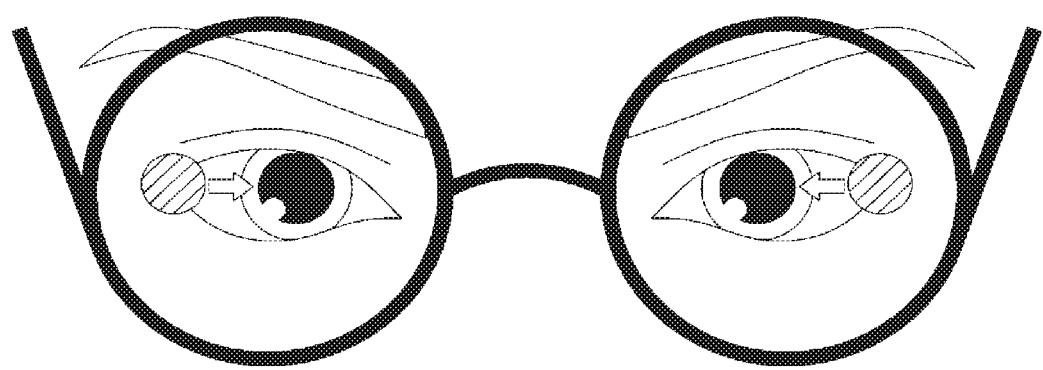
 : nozzle

◯ : nozzle

DEVICE FOR COOLING ANESTHESIA BY CHILLED FLUIDIC COOLING MEDIUM

CROSS-REFERENCE TO RELATED APPLICATIONS

This application claims the benefit of U.S. Provisional Patent Application No. 62/719,695, filed Aug. 19, 2018, and titled "Device for Cooling Anesthesia by Chilled Fluidic Cooling Medium", and U.S. Provisional Patent Application No. 62/756,018, filed Nov. 5, 2018, and titled "Device for Cooling Anesthesia by Chilled Fluidic Cooling Medium." The entire disclosure of the above applications is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The eye is one of the most sensitive areas of the human body. Many ophthalmic medical procedures can cause pain and discomfort for a long period of time, even after patients leave the hospital. For example, the pain at the cornea region associated with photorefractive keratectomy (PRK), laser sub-epithelial keratomileusis (LASEK), or Laser-Assisted In Situ Keratomileusis (LASIK), or the pain at sclera region associated with an intravitreal injection therapy (IVT), use of povidone iodine irrigator, or surgical scission can be quite severe and tends to remain for a few days even after the treatment.

SUMMARY

In general, in one embodiment, a device for cooling a tissue includes a reservoir having fluid therein, a nozzle fluidically connected to the reservoir and configured to pass the fluid from the reservoir therethrough, and a cooling element configured to cool the fluid from the reservoir such that it exits the nozzle at a temperature of between −100° C. and 15° C.

In general, in one embodiment, a hand-held or wearable device for cooling tissue of an eye of a patient includes a reservoir having fluid therein, a support connected to the reservoir and configured to be positioned on a face of the patient, a nozzle positioned proximate to the support and fluidically connected to the reservoir, a cooling element configured to cool the fluid from the reservoir such that it exits the nozzle at a temperature of between −100° C. and 15° C., and an ultrasonic vibrator positioned near the nozzle and configured to generate mist from at least part of the fluid. The nozzle is configured to pass the fluid from the reservoir onto a surface of the eye.

This and other embodiments can include one or more of the following features. The temperature can be between −10° C. and 10° C. The temperature can be between 0° C. and 15° C. A mass flow rate of the fluid as it exits the nozzle can be between 5 and 500 mg/sec. A cooling power of the fluid can be greater than or equal to 0.3 W. The fluid can include a fluid particle that has a volume smaller than 1 mm³. The device can further include a pump configured to pump fluid from the reservoir to the nozzle. The pump can be a manual pump. The cooling element can includes one or more Peltier modules. The total cooling power of the one or more Peltier modules can be between 0.3 W and 100 W. The cooling element can include a vapor compression chiller. The cooling element can include a Joule-Thomson cooler. The cooling element can include a Stirling cycle cooler. The cooling element can include a passive cooling element. The device can further include a temperature sensor configured to detect a temperature of the fluid at the nozzle. The device can further include a controller configured to regulate the cooling element based upon the detected temperature. The fluid may not include a pharmacological anesthetic. The reservoir and cooling element can be part of a hand-held elongate body configured to be held by the user. The device can further include a cone-shaped end piece around the nozzle. The cone-shaped end piece can be configured to be positioned on tissue outside of the patient's eye while maintaining the nozzle spaced away from the eye. The reservoir and cooling element can be part of a device configured to be worn by the user. The device configured to be worn by the user can be a pair of eyeglasses.

In general, in one embodiment, a method of anesthetizing the ocular tissues includes applying a chilled fluid directly onto the surface of the eye so as to anesthetize the cornea or sclera, the chilled fluid is at a temperature of between −100 and 15 degrees Celsius.

This and other embodiments can include one or more of the following features. The fluid can be applied off-axis relative to a central axis of the cornea. The temperature can be between −10° C. and 10° C. The temperature can be between 0° C. and 15° C. A mass flow rate of the fluid as it exits the nozzle can be between 5 and 500 mg/sec. A cooling power of the fluid can be greater than or equal to 0.3 W. The fluid can include a fluid particle that has a volume smaller than 1 mm³. The fluid may not include a pharmacological anesthetic. The method can further include generating mist from the fluid in the reservoir.

BRIEF DESCRIPTION OF THE DRAWINGS

So that the manner in which the above recited features can be understood in detail, a more particular description of the described technology, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3 shows an exemplary cooling device including Peltier modules that are cooled by a heatsink.

FIGS. 7A-7E show an exemplary cooling device that is shaped as eye glasses including one or more eyepiece.

DETAILED DESCRIPTION

Generally, a layer of an eye that is treated by PRK, LASEK, or LASIK may be positioned underneath a protective artificial device (e.g., bandage lens) or an outer surface of the eye (e.g., underneath an outer epithelial layer (flap) of the eye). As a result, it can be difficult to deliver of pharmacological anesthetic agents to the underlayer. In addition, pharmacological anesthetics are not adequate to control the prolonged post-treatment pain, which may continue for more than 10 hours, as their frequent use is known to slow down cornea recovery. Accordingly, improvements are needed to reduce pain without the adverse effects of pharmacological anesthetics after ophthalmic procedures.

Described herein are devices and methods for cooling target mucocutaneous (e.g., the cornea or sclera of the eye) or cutaneous (e.g., skin) tissues to induce anesthesia and analgesia. The devices and methods described herein can be used after treatment of the target tissue, e.g., after ophthalmic surgeries such as PRK, LASEK, LASIK, or IVT. Further, the devices and methods can use fluid as a cooling medium for cooling and thereby anesthetizing the target tissue. Such a fluidic cooling medium can cool sub-tissues (e.g., the lower layers of cornea or sclera) with the minimum mechanical stimulus to sensitive and/or treated tissue, thereby allowing for effective and comfort anesthetizing of the tissue.

Figure 1:
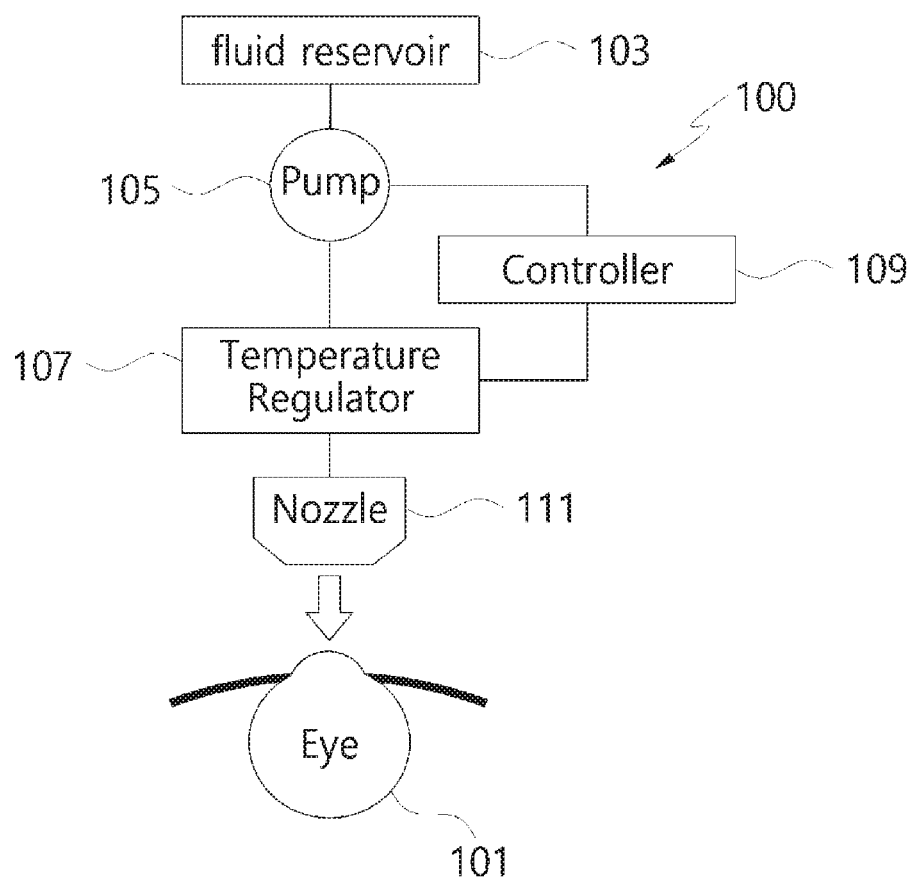
FIG. 1 shows a schematic of an exemplary cooling device positioned so as to deliver cooling medium to the eye.

FIG. 1 shows a schematic of an exemplary cooling device 100 positioned so as to deliver cooling medium to the eye 101. The device 100 includes a fluid reservoir 103, a pump 105, a temperature regulator 107, a controller 109, and a nozzle 111. The reservoir 103 can hold a fluid that is configured to be cooled for application to the eye 101. The pump 105 can be, for example, a manual pump that the user pressurizes by hand or an automatic pump such as capillary pump, rotary pump, linear pump, or peristatic pump. The temperature regulator 107 can be configured to use a cooling method to cool the fluid pumped from the fluid reservoir 103. The temperature regulator 107 can be an active cooling regulator 107 that uses an active cooling element (e.g., Peltier cooler, vapor compression chiller, Joule-Thomson cooler, or Stirling cycle cooler) or a passive cooling element (e.g., ice, dry ice) to cool fluid from the reservoir 103 as it moves to the nozzle 111. Further, the nozzle 111 can dispense the chilled fluid (as a liquid or mist) to the target area (i.e., onto the eye 101). The nozzle can have at least one hole, through which the chilled fluid is delivered. Further, the controller 109 can be configured to control the pump 105 and/or the temperature regulator 107, e.g., upon activation by the user.

The device 100 can be configured to cool the target area (e.g., cornea) of the eye 100 by chilled fluid that is at a temperature below 15° C. (measured at the nozzle 111 or the temperature regulator 107).

The chilled fluid can be, for example, water, oil, saline solution, tear-replacing solution, lubricating solution, or a solution containing a steroid, an antihistamine, a sympathomimetic, a beta receptor blocker, a parasympathomimetic, a parasympatholytic, a prostaglandin, a nonsteroidal anti-inflammatory drug (NSAID), an antibiotic, a povidone-iodine, an antifungal, a topical anesthetic, or a mydriatic agent. In some embodiments, the chilled fluid does not include a pharmacological anesthetic (i.e., only the chilled fluid acts to anesthetize the tissue). In other embodiments, the chilled fluid can include a pharmacological anesthetic and its cold temperature synergistically anesthetizes the target tissues with a pharmacological anesthetic.

In some embodiments, the temperature regulator and the fluid reservoir can be combined. For example, a combined passive regulator/ reservoir can include an insulative fluid container with a pre-cooled substance such as ice, dry ice, or pre-chilled fluid that melts and is then supplied to the nozzle.

In some embodiments, the temperature regulator and the nozzle can be combined. For example, the nozzle can simultaneously chill and dispense fluid.

In some embodiments, the nozzle can mechanically couple with a vibrator and atomize chilled fluid to small mist droplets. For example, the nozzle can simultaneously atomize and dispense the chilled fluid.

In some embodiments, the fluid in the fluid reservoir can be pressurized or can be driven by gravity such that no pump is necessary.

In some embodiments, the fluid reservoir can be an eye drop bottle (e.g., a commercially available eye drop bottle) or replaceable liquid bottle that is configured to mechanically couple and decouple with the cooling device.

In some embodiments, the chilled fluid can be air, and the fluid reservoir can be an open inlet of air.

In some embodiments, the temperature regulator can increase its temperature to evaporate and thereby remove residual fluid inside the fluid channel.

Figure 2A:
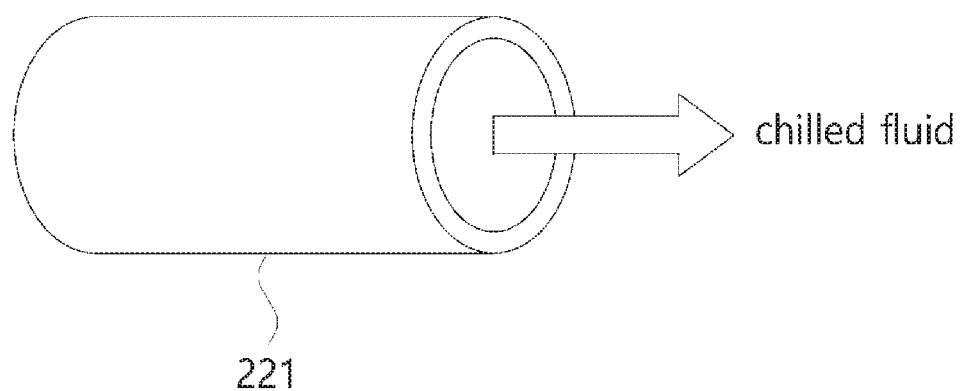
FIGS. 2A-2D show an exemplary cooling transfer channel.
Figure 2B:
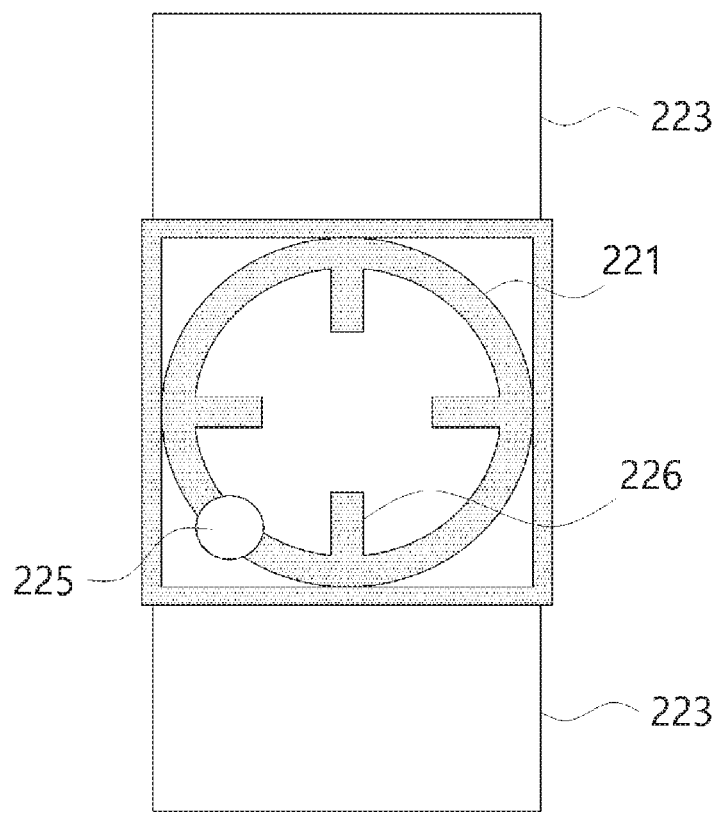
Figure 2C:
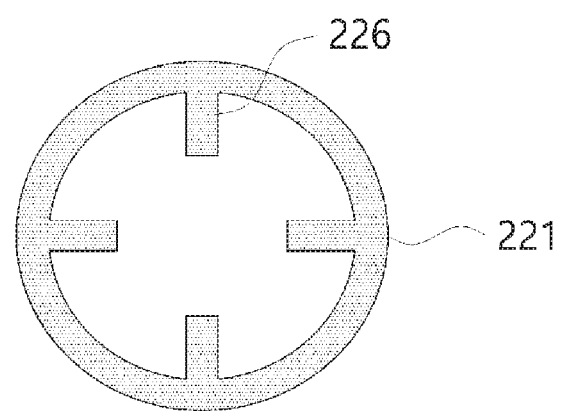
Figure 2D:
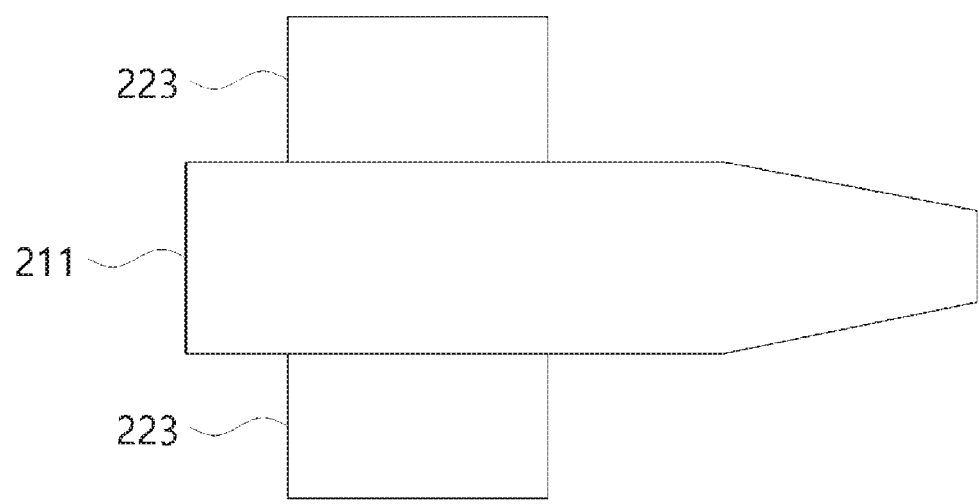

In some embodiments, referring to FIGS. 2A-2D, a temperature regulator can include a cooling transfer channel 221 that can both guide fluid from the reservoir therethrough and transfer cooling energy from the temperature regulator to the fluid. As shown in FIG. 2B, in some embodiments, the channel 221 can be thermally coupled with the cold side of one or more Peltier modules 223 (which can be used as an active cooling element). Further, a temperature sensor 225 can be positioned within or just outside of the cooling transfer channel 221 to regulate the temperature of fluid therein. The temperature sensor 225 can be configured to detect the temperature of the channel 221 and/or the fluid within the channel. As shown in FIG. 2C, in some embodiments, the inner circumference of the channel 221 can have fins 226, divots, or other features that can increase the surface area of the channel 221 to enhance the heat transfer between the fluid and the channel 221. In some embodiments, the cooling transfer channel 221 can have plurality of fluid channels such as circular or polygonal holes to increase the surface area of the channel 221. Further, referring to FIG.

2D, in some embodiments, the nozzle 211 can function as the cooling transfer channel with the Peltier modules 223 therearound. In some embodiments, the cooling transfer channel 221 can be made of a thermally conductive material having a thermal conductivity greater than 10 W/m-K. For example, the cooling transfer channel can be made of metal such as copper or aluminum, or the alloy of copper or aluminum. The cooling transfer channel can be encapsulated by a thermally insulating material having a thermal conductivity lower than 5 W/m-K, such as elastomer, polymer, plastic foam, or woven fibers.

Referring to FIG. 3, in some embodiments, a cooling device 300 can include Peltier modules 323 that are cooled by a heatsink 331. In some embodiments, the heatsink 331 can be cooled by forced air convection with one or more fans 333 or by natural air convection without a fan. In other embodiments, the heatsink 331 can be cooled by liquid. The Peltier modules 323 and the heatsink 331 can locate remotely to each other with a heat pipe 335 that thermally couples the Peltier modules 323 and the heatsink 331. In such configuration, heat can be actively pumped from the chilled liquid by the Peltier modules 323 via the cooling transfer channel, can be ejected to the heatsink 331 via the heat pipe 335, and can finally be removed by air flow through the heatsink 331. The fluid reservoir 303 can thus supply chilled fluid through the cooling transfer channel or the combined cooling transfer channel/nozzle 311.

Figure 4:
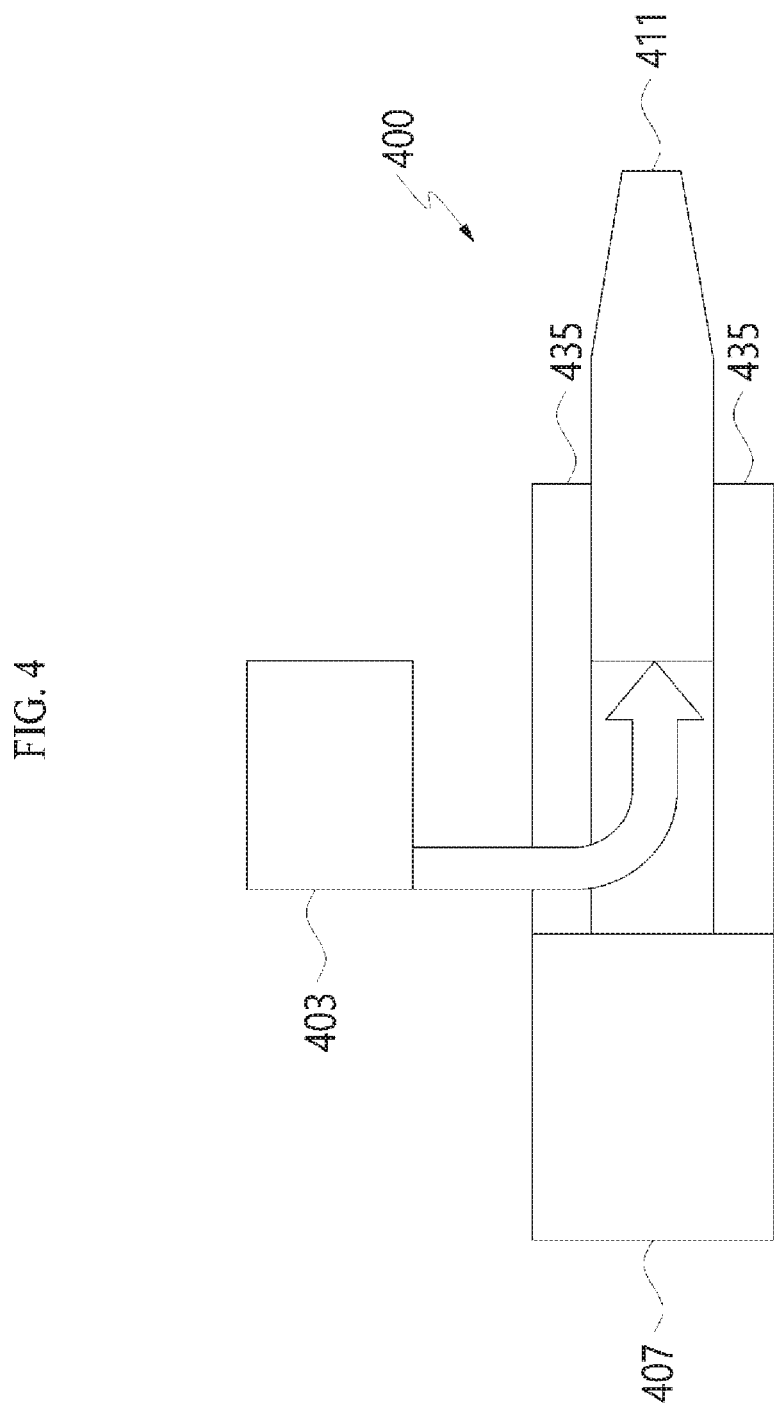
FIG. 4 shows an exemplary cooling device including a passive temperature regulator.

Referring to FIG. 4, in some embodiments, a cooling device 400 can include a passive temperature regulator 407, e.g., with ice cubes, dry ice, or chilled liquid therein. The passive temperature regulator 407 can be connected to the cooling transfer channel or a combined cooling transfer channel/nozzle 411 via heat pipe 435. In such configuration, heat can be passively transferred from the chilled liquid to the passive temperature regulator 407 via the heat pipe 435, and can be removed by ice cubes, dry ice, or chilled liquid in the passive temperature regulator 407. The fluid reservoir 403 can thus supply chilled fluid through the cooling transfer channel or the combined cooling transfer channel/nozzle 411 (which can be cooled by the passive temperature regulator 407 via the heat pipe 435).

Figure 5:
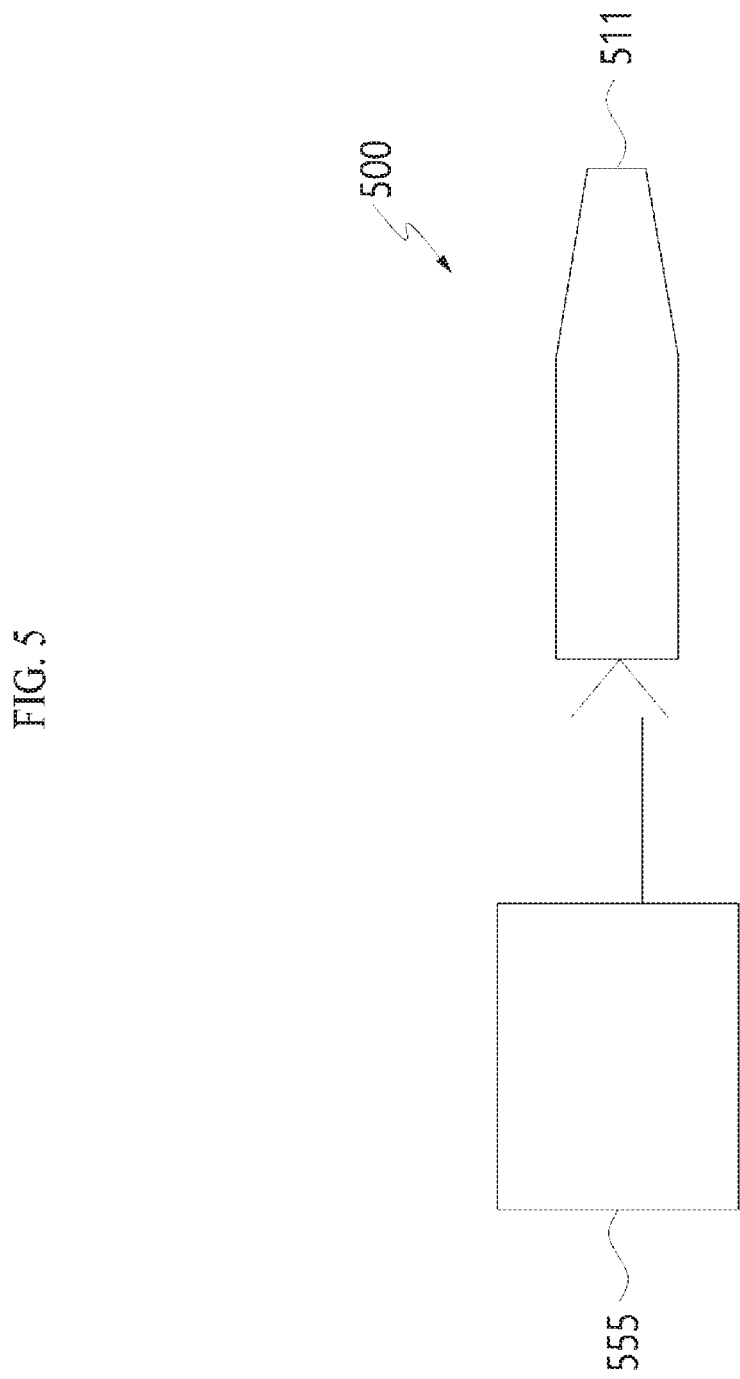
FIG. 5 shows an exemplary cooling device including a combined feature that functions as a passive temperature regulator and a fluid reservoir.

Referring to FIG. 5, in some embodiments, a cooling device 500 can include a combined feature 555 that functions as a passive temperature regulator and a fluid reservoir. For example, combined feature 555 can be an insulated compartment having ice cubes or chilled liquid therein. As fluid melts from the combined feature 555 or chilled liquid comes from the combined feature 555, the fluid can be transferred into the cooling transfer channel or the combined cooling transfer channel/nozzle 511 for delivery to the target area.

Figure 6:
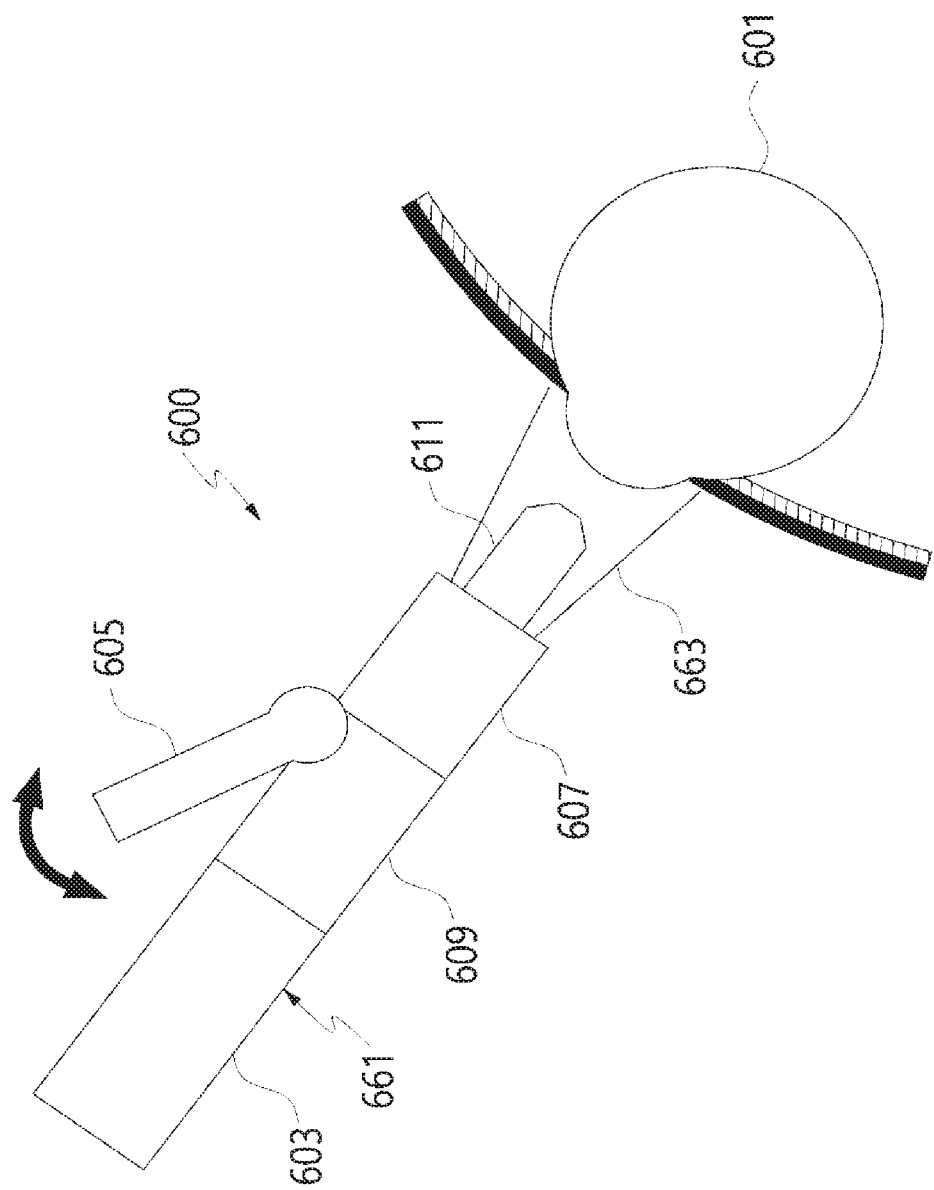
FIG. 6 shows an exemplary cooling device having an elongated handheld form.

Referring to FIG. 6, in some embodiments, the cooling device 600 can have an elongated handheld form. For example, the reservoir 603 can be positioned axially aligned with the controller 609, which can be axially aligned with the temperature regulator 607 and nozzle 611. A pump 605 can be configured to be grasped and pulled by one or more fingers (e.g., in the direction of the arrows) as the palm holds the rest of the elongate body 661. The user can thus hold the elongate body 661 while directing the nozzle 611 towards the eye 601. As the pump 605 is activated by the user, fluid can move from the reservoir 603 through the nozzle 611 onto the eye to cool the tissue of the eye 601. In some embodiments, the device 600 can include a cone-shape front piece 663 configured to sit on the skin around the eye 601 to help center the nozzle 611 within the target area or to maintain the distance between the nozzle 611 and the target area. The front piece 663 can, for example, be disposable and detachable from the rest of the elongate body 661.

In some embodiments, the chilled liquid in the temperature regulator 107, the nozzle 111, or the combined cooling transfer channel/nozzle 311 can be pressurized by the pump 105 and thereby have a pressure greater than atmosphere pressure. Such chilled liquid at a pressure above the atmosphere pressure can have a large pressure drop at the nozzle outlet, and thereby be further cooled down by Joule-Thompson effect, which can lead to the formation of small solid ice particles and therefore provide a greater cooling capacity.

Figure 7A:
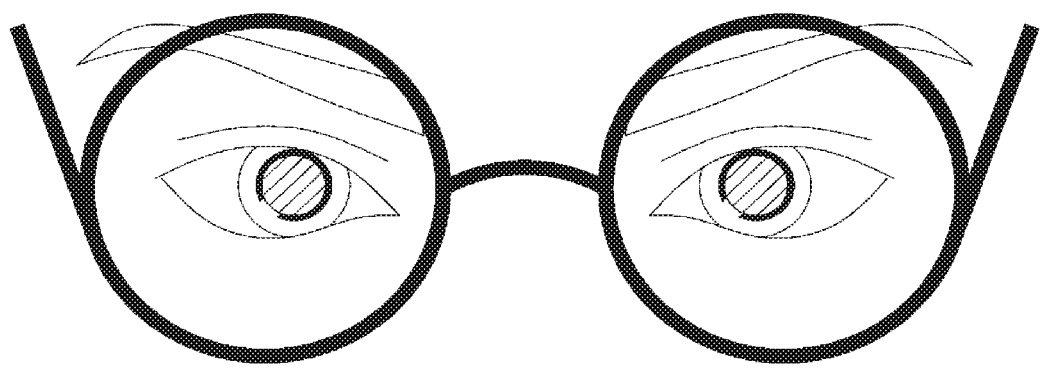
Figure 7B:
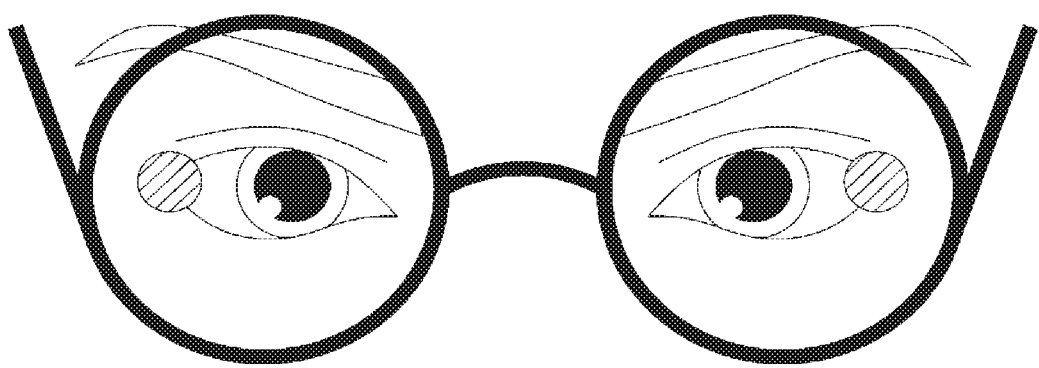
Figure 7D:
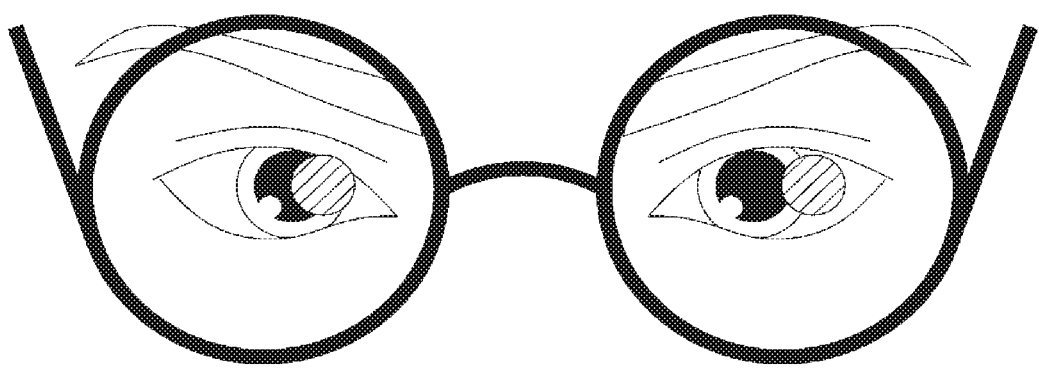
Figure 7E:
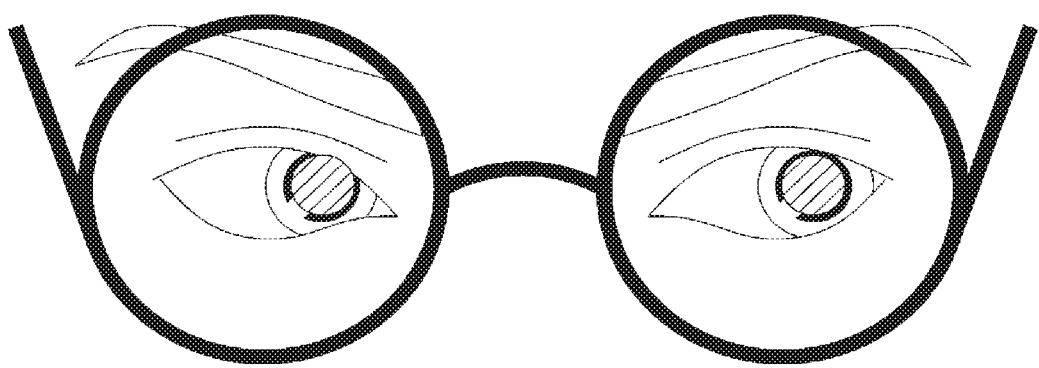

In some embodiments, the cooling devices described herein can be wearable. For example, as shown in FIGS. 7A-7E, the cooling device can be shaped as eye glasses including one or more eyepiece. Further, one or more of the eyepieces can include the nozzles attached thereto to direct cooling fluid towards the eye. For example, FIG. 7A shows a set of glasses where the nozzle is attached to the eyepiece such that the nozzle is centered over the eye (i.e., aligned with the center of the cornea). As another example, referring to FIGS. 7B-7E, the nozzle can be off-axis with respect to the central axis of the cornea to allow for unobstructed sight but can have an aligned direction to the center of the cornea to allow the chilled fluid to be ejected to the center of the cornea. In some embodiments, FIG. 7B shows a stand-by state of the off-axis nozzle, and as shown in FIG. 7C, the off-axis nozzle can be configured to spray mist onto the eye from the nozzle. In other embodiments, FIG. 7D shows other stand-by state of the off-axis nozzle, and as shown in FIG. 7E, the off-axis nozzle can be configured to deliver liquid onto the eye by having the patient look at the nozzle when delivering fluid.

Figure 8A:
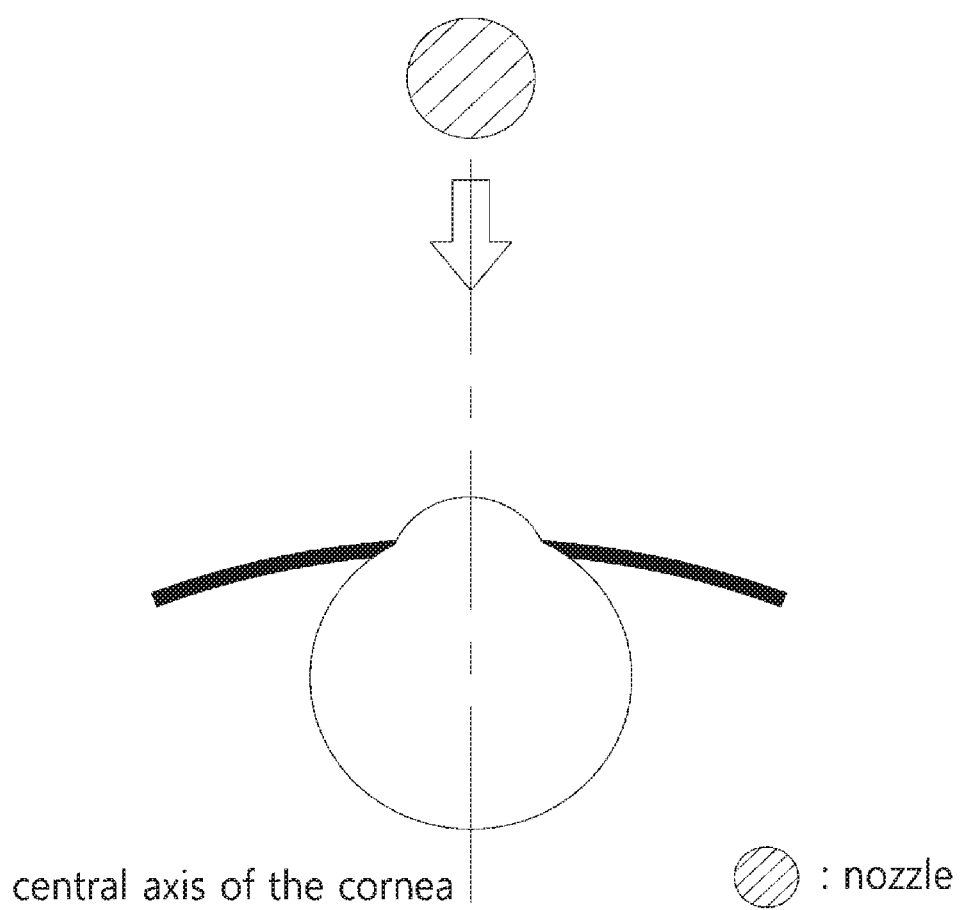
FIG. 8A is a more detailed view of a cooling devices aligned on-axis relative to the central axis of the cornea.
Figure 8B:
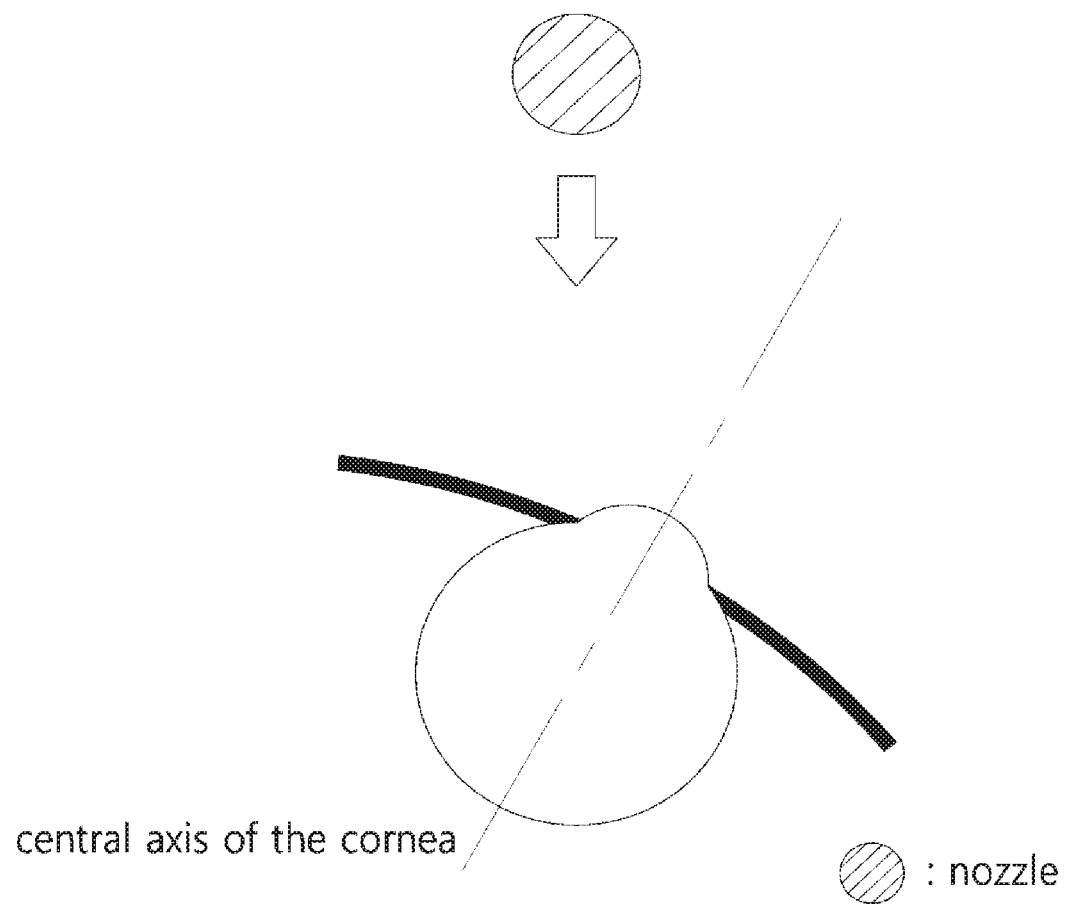
FIG. 8B is a more detailed view of a cooling devices aligned off-axis relative to the central axis of the cornea.

A more detailed view of the cooling devices aligned on-axis (FIG. 8A) and off-axis (FIG. 8B) relative to the central axis of the cornea is shown in FIGS. 8A-8B. Positioning the nozzle off-axis relative to the central axis of the cornea, as shown in FIG. 8B, can advantageously provide clear sight along the central axis of the cornea. In some embodiments, if the cooling device of FIG. 8B is an elongated handheld device (as shown in FIG. 6), then the cone-shaped front piece can be tilted or angled so as to still sit around the eye, but so as to angle the nozzle and elongated device off-axis relative to the central axis of the cornea. In other embodiments, if the cooling device of FIG. 8B is wearable (as shown in FIGS. 7A-7E), then the nozzle can be connected to the eyeglasses or lenses in an off-center position.

Figure 9:
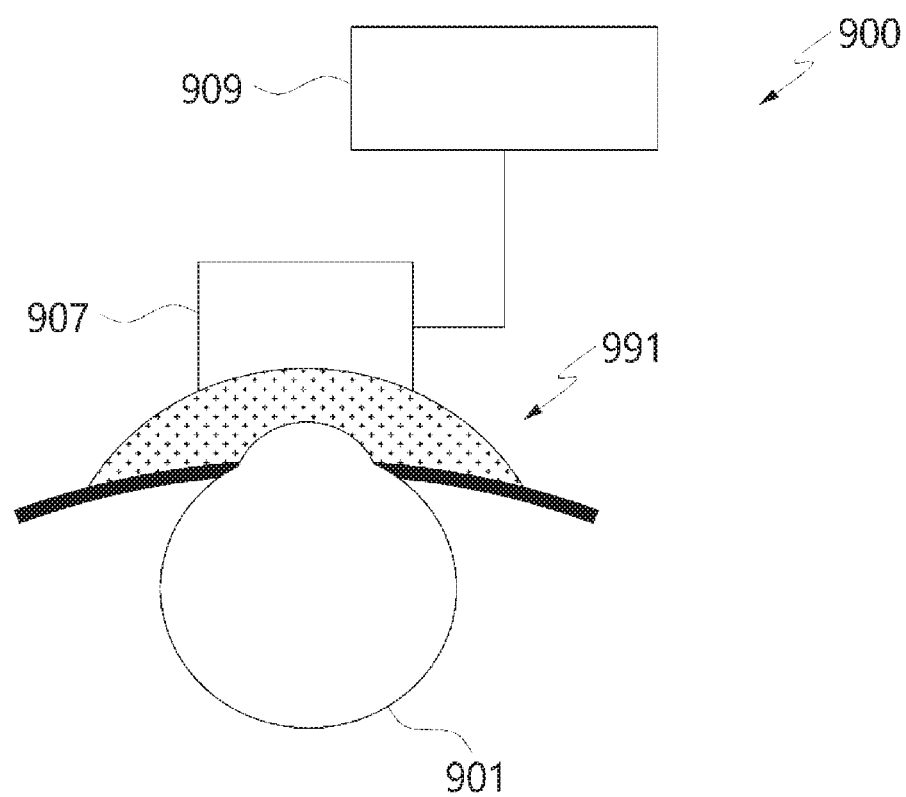
FIG. 9 shows an exemplary cooling device including a chamber configured to sit directly on the eye.

Referring to FIG. 9, in some embodiments, the device 900 can include a chamber 991 configured to sit directly on the eye 901 (i.e., such that one side of the closed chamber is formed by the eye). For example, the chamber 991 can have a shape similar to swimming goggles. Cooled fluid in the chamber 991 can be configured to remain or circulate within the chamber to cool the target tissue. In some embodiments, the temperature regulator 907 can be part of the chamber 991. In other embodiments, the temperature regulator 907 can be separate from the chamber 990 (i.e., be attached to the outside thereof as shown in FIG. 9) such that fluid circulates between the chamber 991 and the temperature regulator 907 (i.e., as controlled by the controller 909).

Figure 12:
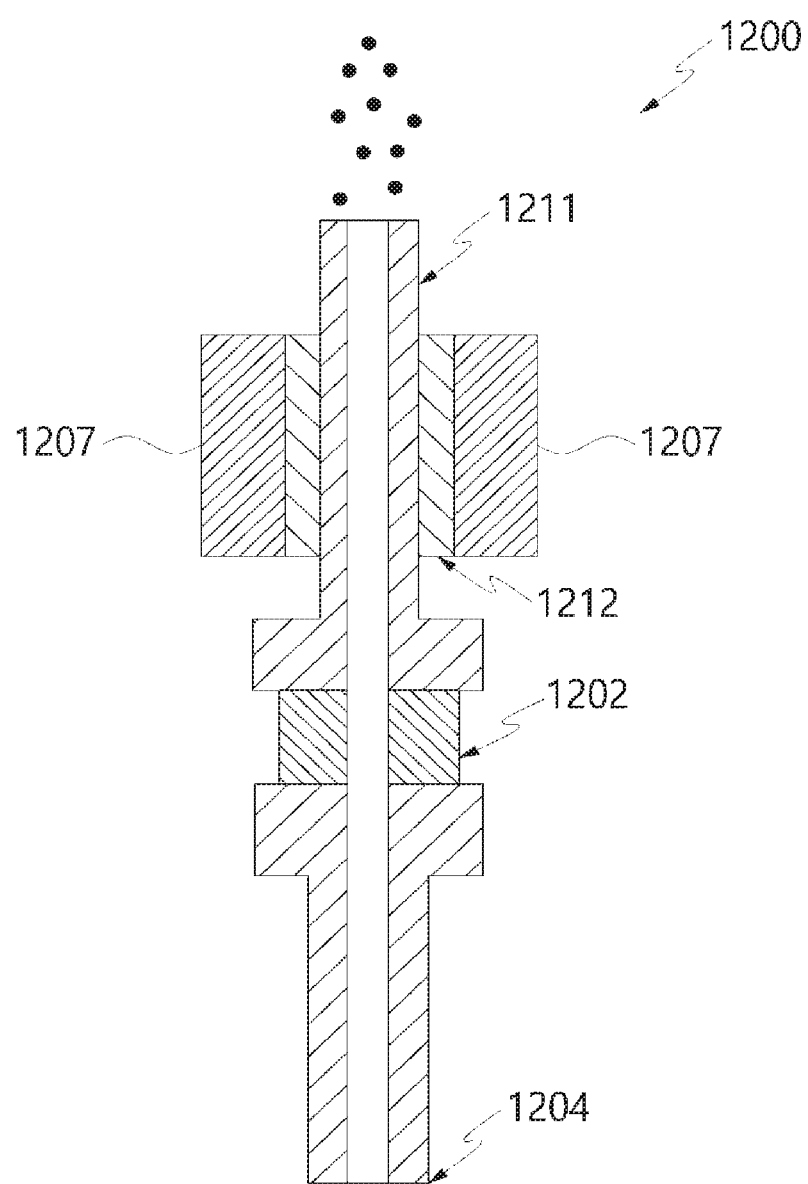
FIG. 12 shows an exemplary cross sectional view of a cooling device.

FIG. 12 shows a cross sectional view of a cooling device. Referring to FIG. 12, in some embodiments, a cooling device 1200 can be configured to provide mist that is generated using an ultrasonic generator 1202. The ultrasonic generator 1202 can generate vibration in the direction of fluid flow so as to vibrate the nozzle 1211. Fluid can thus enter the fluid inlet line 1204, travel through the ultrasonic vibrator 1202, and through the temperature regulator 1207. Further, the fluid can travel through the nozzle 1211 that is thermally coupled to the temperature regulator 1207 and mechanically coupled with the ultrasonic vibrator 1202 to produce small mist droplets at the outlet. The nozzle 1211 can be, for example, a straight nozzle (i.e., non-tapered) and can include two surfaces that are parallel to one another. The two parallel surfaces can be in contact with the Peltier modules and enable an installation pressure by mechanical fasteners normal to the cold surface of the Peltier modules. In some embodiments, a temperature sensor can monitor the temperature of the nozzle and maintain the fluid or mist at the desired temperature. Further, in some embodiment, the temperature regulator 1207 can include an interface layer 1212 therein that provides thermal coupling between the temperature regulator 1207 and the nozzle 1211 and that provides vibrational damping between the temperature regulator 1207 and the nozzle 1211.

Figure 11A:
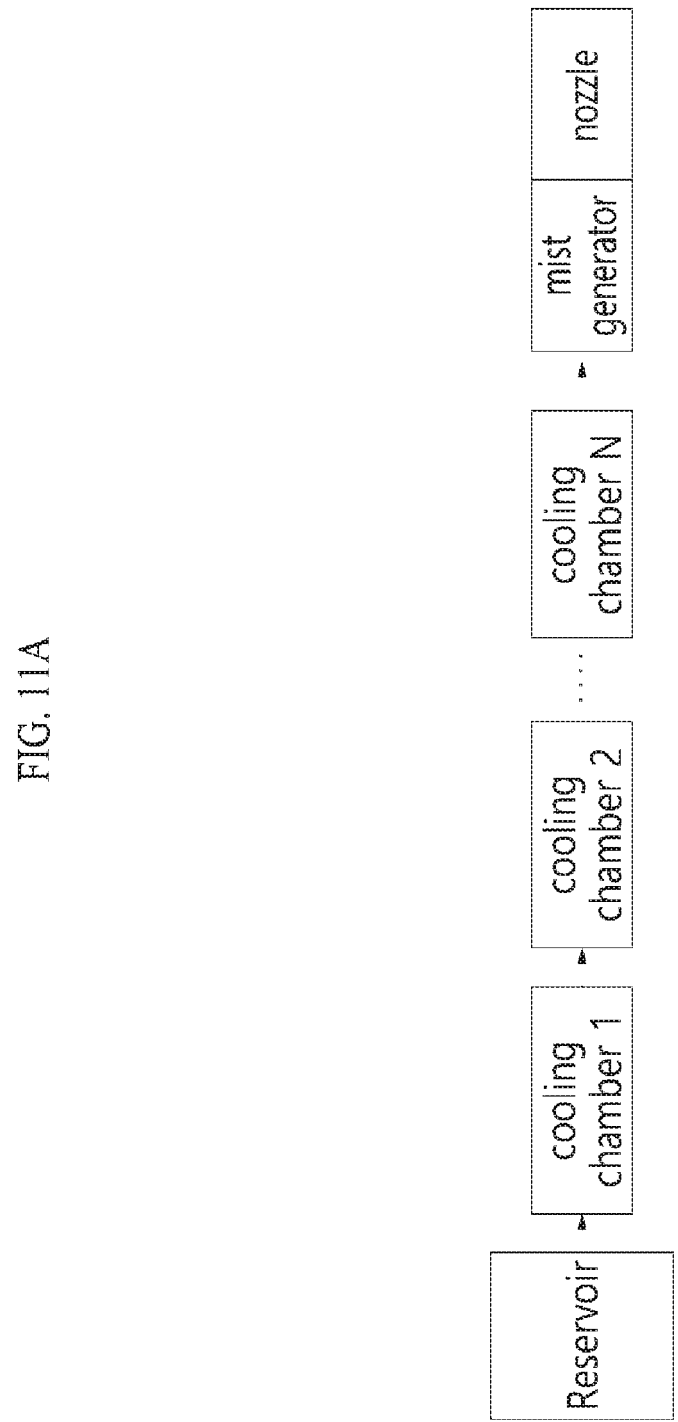
FIGS. 11A-11B show an exemplary cooling device including multiple cooling chambers.
Figure 11B:
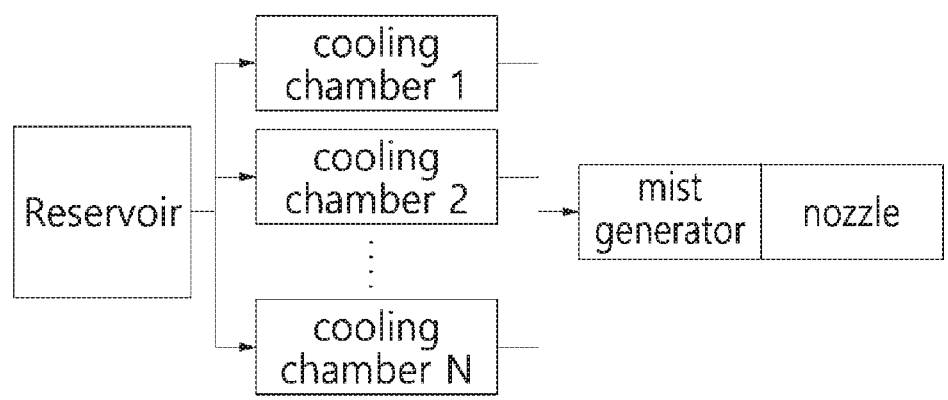

FIGS. 11A-11B show an exemplary cooling device including multiple cooling chambers. According to the some embodiments, the cooling device includes reservoir, multiple cooling chambers, a mist generator and nozzle. Further, the plurality of cooling chambers can be connected together in series (see FIG. 11A) or in parallel (see FIG. 11B) or on a combination of series and parallel. Depending on the mass rate of the chilled fluid needed, the power can be controlled by using a set number of cooling chambers from the connected cooling chambers. The fluid stored in reservoir flow into multiple cooling chambers, the mist generator and nozzle sequentially. The mist generator and nozzle can be a cooling chamber being coupled with Peltier modules.

Figure 10A:
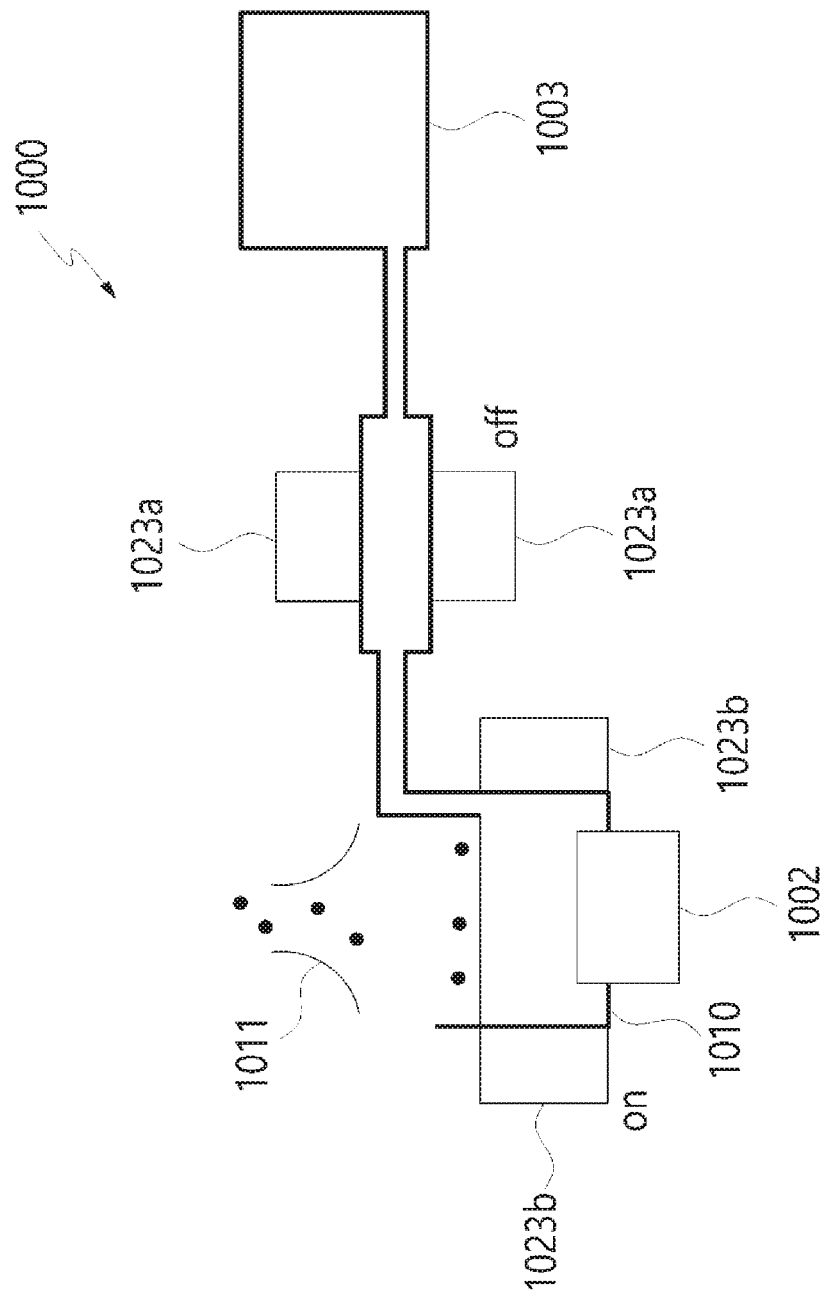
FIGS. 10A-10B show an exemplary cooling device including multiple Peltier cooling chambers that are connected in series.
Figure 10B:
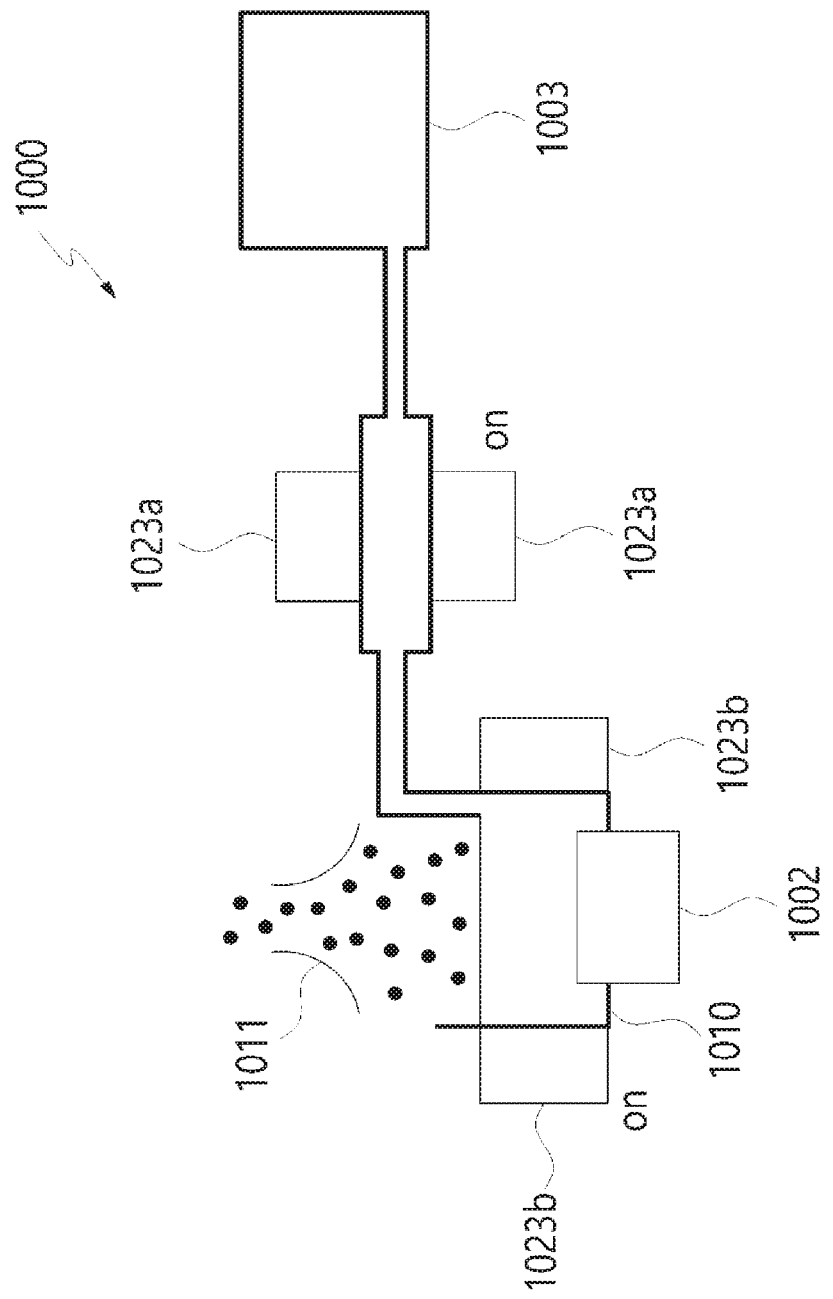

FIGS. 10A-10B show an exemplary cooling device 1000 multiple Peltier cooling chambers 1023*a,b* can be connected in series for the delivery of chilled mist out of nozzle 1011. A reservoir 1003 can be connected to a Peltier chamber 1023*a*, which can be connected in series to a second Peltier chamber 1023*b*. The second Peltier chamber 1023*b* can be positioned around a chilled liquid chamber 1010 with an ultrasonic atomizer 1002 therein. Referring to FIG. 10A, the cooling device 1000 can have a low power mode in which only one of the cooling chambers (e.g., chamber 1023*b*) is on while the other cooling chamber (e.g., chamber 1023*a*) is off. Additionally, in the low power mode, the ultrasonic atomizer 1002 can be set at lower level so as to create mist at a lower flow rate. Referring to FIG. 10B, the cooling device 1000 can have a high power mode in which both cooling chamber 1023*a* and 1023*b* are on. Additionally, in the higher power mode, the ultrasonic atomizer 1002 can be set to a higher level so as to create higher flow rate of the mist. In some embodiments, a fan can additionally be used to create a higher flow rate.

Figure 15A:
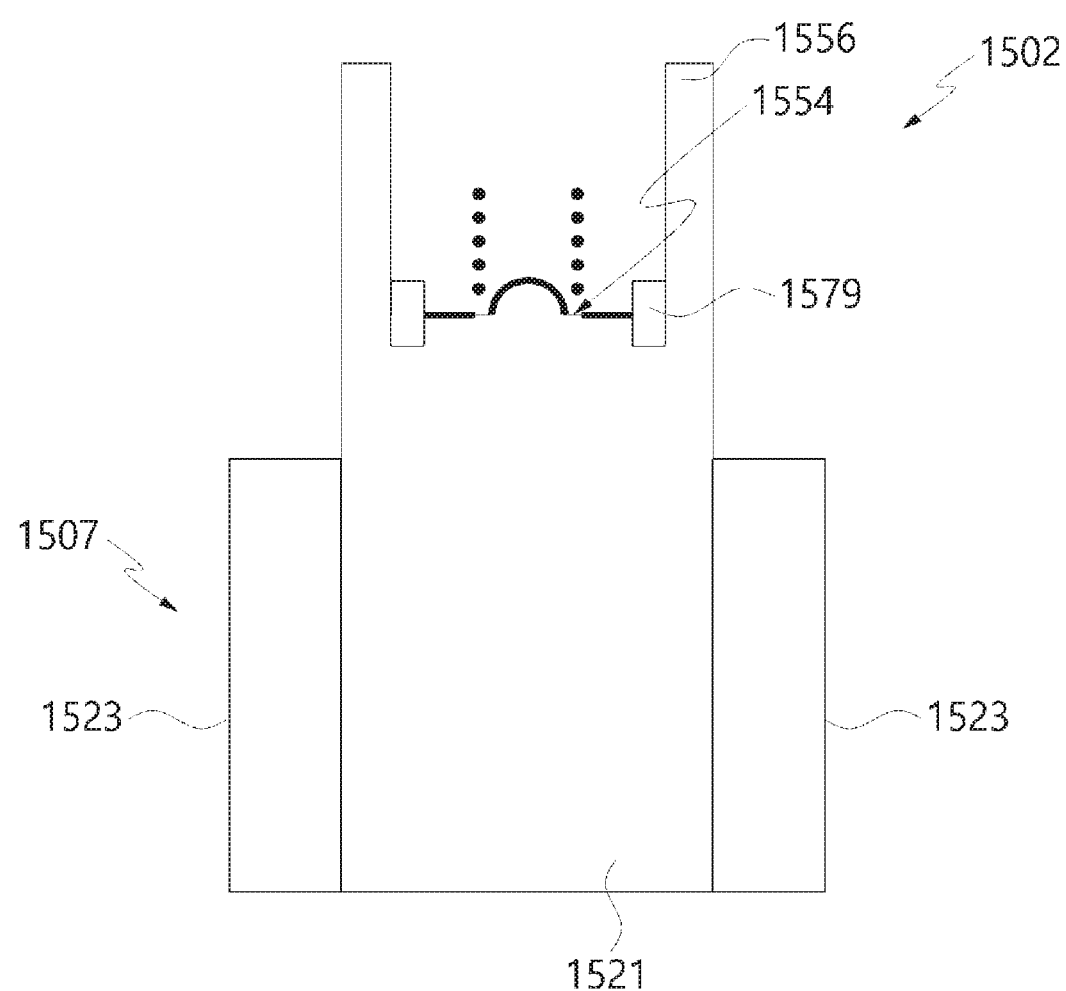
FIG. 15A shows an exemplary cooling device including an ultrasonic atomizer having a vibrating plate and one or more holes.
Figure 15B:
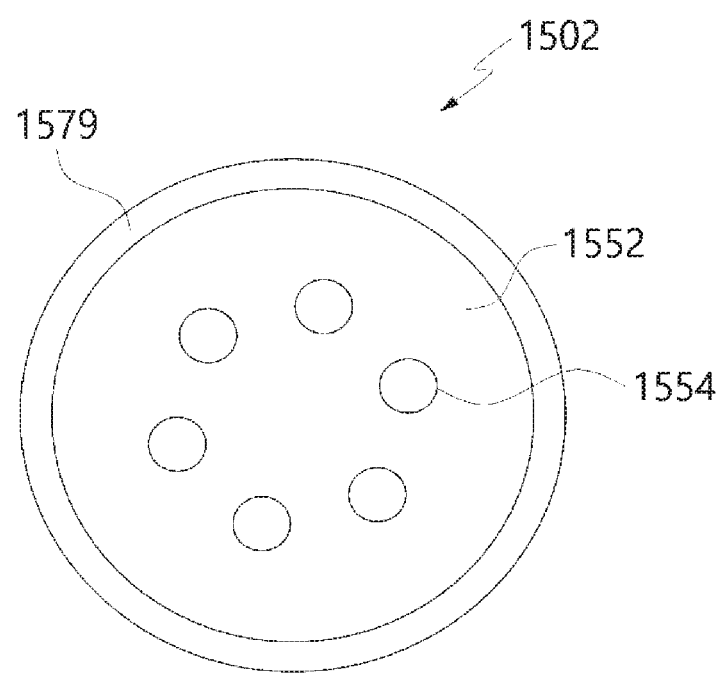
FIG. 15B shows a magnified top view of an ultrasonic atomizer.

FIG. 15A shows an exemplary cooling device including an ultrasonic atomizer having a vibrating plate and one or more holes. FIG. 15B shows a magnified top view of an ultrasonic atomizer. Referring to FIGS. 15A-15B, in some embodiments, the ultrasonic atomizer 1502 can have a vibrating plate 1552 and one or more holes 1554, through which chilled fluid from the cooling chamber can pass and be atomized to mist droplets. The vibrating plate may be referred to as a vibrating mesh. The ultrasonic atomizer 1502 can be thermally coupled with the temperature regulator 1507 (including a Peltier module 1523 and cooling transfer channel 1521 with a plurality of channels to increase surface area). More specifically, an electrically insulating coupling gasket 1579 can be installed between the ultrasonic atomizer 1502 and the temperature regulator 1507 to seal the chilled fluid. The electrically insulating coupling gasket 1579 can have a thermal conductivity larger than 1 W/m-K to thermally couple the atomizer 1502 and the temperature regulator 1507, thereby allowing the ultrasonic atomizer 1502 to have a temperature within +/−10° C. of that of the temperature regulator 1507. In some embodiments, the electrically insulating coupling gasket 1579 can have a durometer hardness less than Shore A90 to facilitate the sealing of the chilled fluid therein. For such configuration, the vibrating plate 1552 of the ultrasonic atomizer 1502 can function as both the nozzle and the ultrasonic atomizer. The temperature regulator can further couple with an extended mist channel 1556, which can keep surrounding warm air out from the chilled mist and thereby maintain the temperature of the chilled mist at an extended distance. The extended mist channel 1556 can be made of a thermally conductive material having a thermal conductivity larger than 10 W/m-K and can be covered by a thermally insulating material having a thermal conductivity lower than 5 W/m-K.

Figure 13:
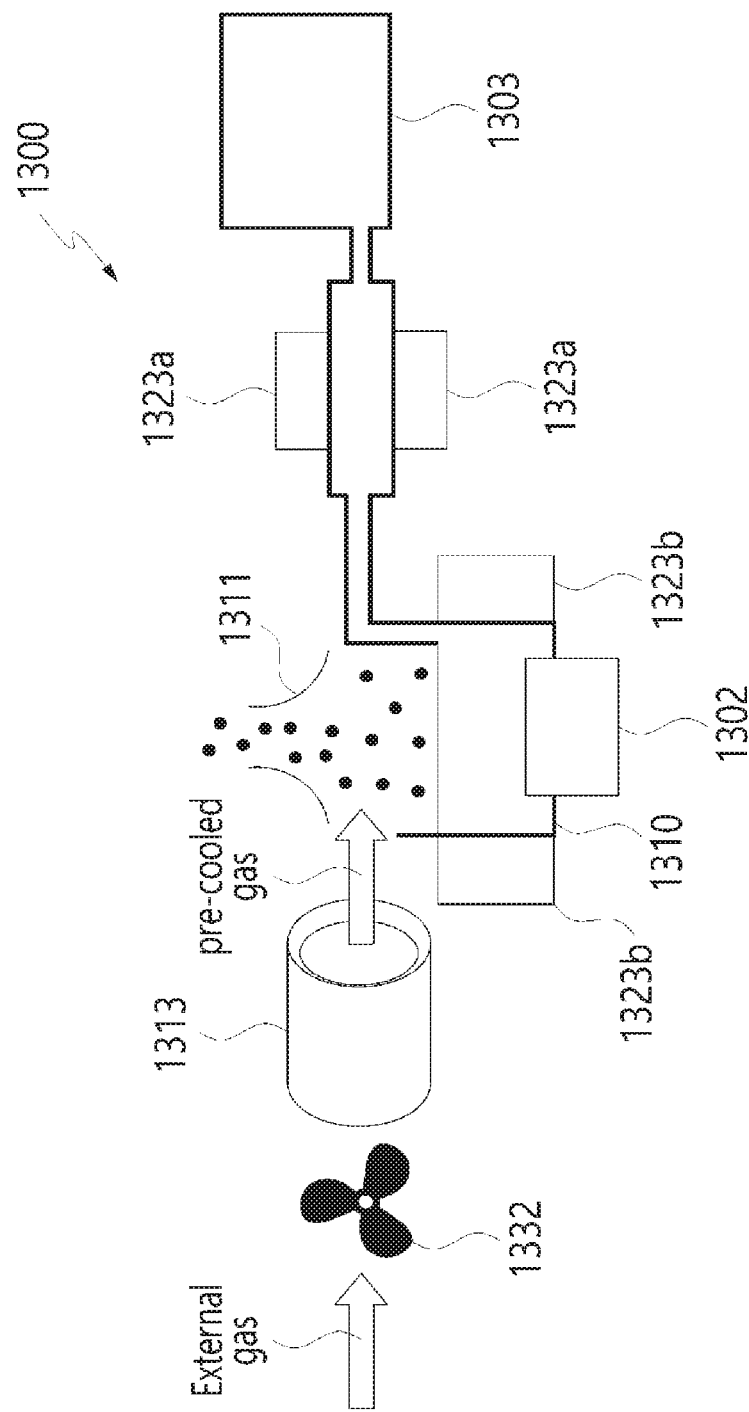
FIG. 13 shows an exemplary cooling device including a fan and additional cooling transfer channel.

Referring to FIG. 13, in some embodiments, mist from the chilled liquid can be mixed with pre-cooled gas or can be collimated by pre-cooled gas to keep surrounding warm air out from the chilled mist and thereby to maintain the low temperature of the chilled mist at an extended distance. The pre-cooled gas can be cooled, for example, via a Peltier cooler, a vapor compression chiller, a Joule-Thomson cooler, or a Stirling cycle cooler) or passive cooling. For example, cooling device 1300 includes a fan 1332 and additional cooling transfer channel 1313. External gas can thus enter the device 1300, travel via the fan through the cooling transfer channel 1313, and mix with chilled mist from the reservoir 1303, cooling chambers 1323*a/b* and chilled liquid chamber 1310 to exit through the outlet 1311 at a higher speed.

Figure 16A:
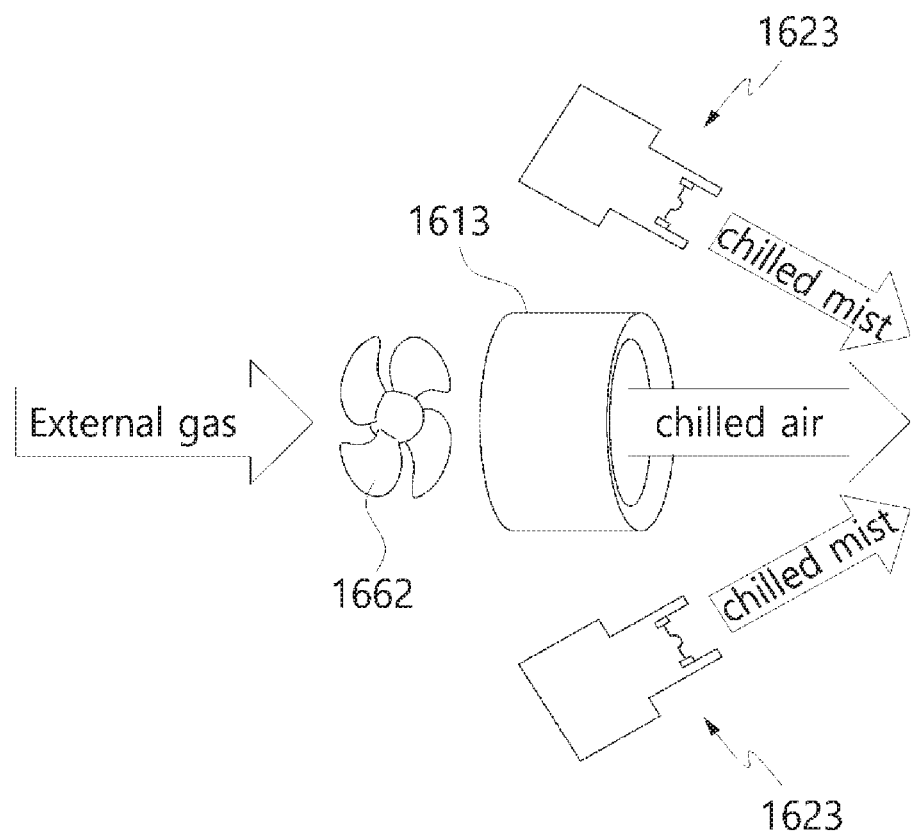
FIGS. 16A-16B show an exemplary cooling device including a fan and additional cooling transfer channel.
Figure 16B:
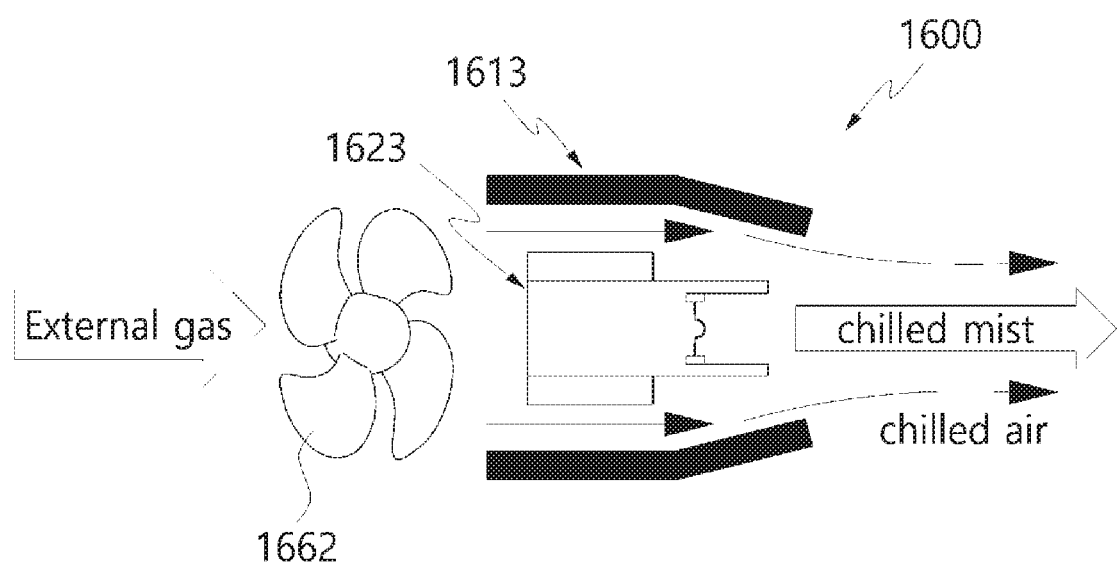

Similarly, referring to FIGS. 16A, in some embodiments, external gas can enter the device 1600, travel via the fan 1662 through the cooling transfer channel 1613, and collimate with chilled mist from the reservoir and cooling chambers 1623 exit through the outlet at a higher speed. As shown in FIG. 16B, in other embodiments, chilled air can be used to keep outside warm air away from the chilled mist and therefore maintain a low temperature of the mist.

In some embodiments, the cooled gas can have a temperature lower than the freezing point of the fluid (e.g., between 0° C. and −100° C., such as between 0° C. and −75° C., such as between 0° C. and −10° C.), which may change the phase of the mist from liquid to solid (ice) and therefore can increase the cooling capacity of the chilled fluid with latent heat.

In some embodiments, electric current with an opposite polarization can feed the Peltier modules of the temperature regulator. With such current of opposite polarization, the Peltier modules heat the fluid cooling channel 221 and thereby fluid therein. In this configuration of the opposite polarization, the fluid applied to a target area can have a high temperature, aiming at different therapeutic effects such as extensibility of collagen tissues; decreasing joint stiffness; reducing pain; relieving muscle spasms; reducing inflammation, edema, and aids in the post acute phase of healing; and increasing blood flow. In some embodiments, the opposite polarity can be applied to evaporate and hence remove residual fluid in the fluid channel.

The devices described herein can cool the tissue, e.g., the entire of thickness of the cornea, to between 8 and 12° C. A temperature within this range is effective in minimizing chronic pain. It should be noted that the calculations below can be similarly applied to find the parameters such as mass flow rate, cooling power, and temperature of the chilled liquid for the cooling of the sclera region or other areas of the human body.

Figure 14:
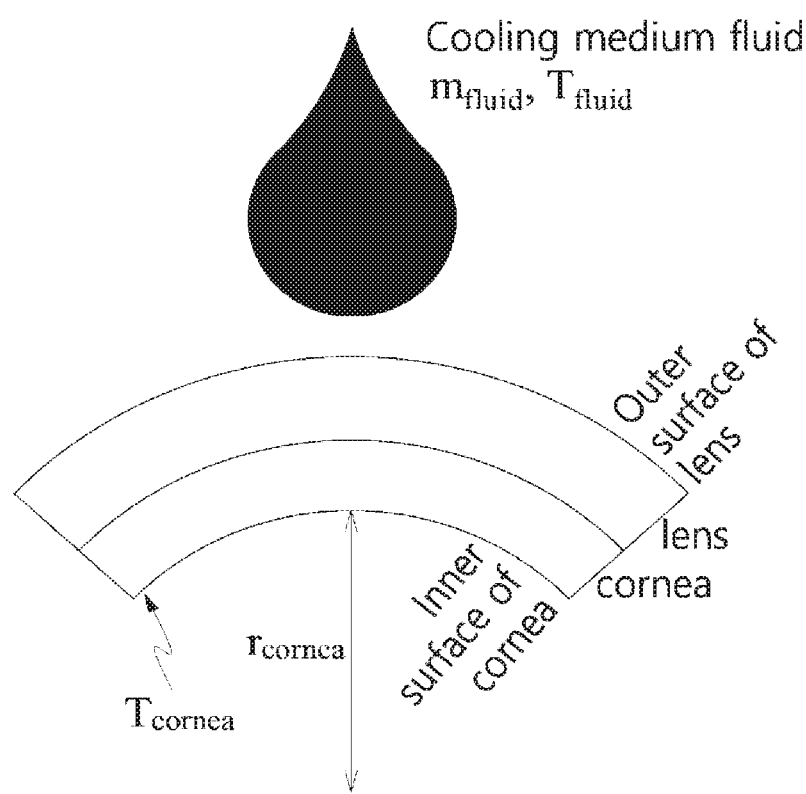
FIG. 14 shows an outer surface of cornea covered by a protective lens that facilitates its recovery.

As shown in FIG. 14, the outer surface of cornea can be covered by a protective lens that facilitates its recovery. The thickness and thermal conductivity of the protective lens are $t_{lens}$ and $k_{lens}$, respectively. Values for the applicable variable are shown below in Table 1.

TABLE 1

| | Symbols | Literature values |
|---|---|---|
| cornea thermal conductivity (W/m-K) | $k_{cornea}$ | 0.58 |
| cornea thickness (m) | $t_{cornea}$ | 0.0005 |
| cornea inner radius (m) | $r_{cornea}$ | 0.0068 |
| temperature at the inner surface of cornea (° C.) | $T_{cornea}$ | a value between 8 and 12° C., say 12° C. for minimum cooling power |
| bandage lens thermal conductivity (W/m-K) | $k_{lens}$ | 0.9 |
| bandage lens thickness (m) | $t_{lens}$ | 0.0005 |
| heat transfer coefficient at the inner surface of cornea (W/m²-K) | $h_{cornea}$ | 65 |
| cooling medium fluid heat capacity (J/g-K) | $c_{fluid}$ | for water, 4.2 |
| cooling medium mass flow rate (g/sec) | $m_{fluid}$ | |
| cooling medium fluid temperature (° C.) | $T_{fluid}$ | |

The governing equation that dictates the balance between body heat from the inner surface of cornea and cooling power provided by the cooling medium fluid is given by Equation 1:

$$q_{fluid} = h_{cornea} A_{cornea}(37 - T_{cornea}) = m_{fluid} c_{fluid}(T_{lens} - T_{fluid})$$ (Equation 1)

where $A_{cornea}$, $T_{lens}$, and $R_{tot}$ are the area of cornea inner surface, temperature at the outer surface of the bandage lens and the total thermal resistance across the cornea and the lens, respectively, and given as:

$$A_{cornea} = \frac{4\pi r_{cornea}^2}{3}$$ (Equation 2)

$$T_{lens} = T_{cornea} - \frac{q_{fluid}}{R_{tot}}$$

$$R_{tot} = \frac{3}{4\pi k_{cornea}} \left( \frac{1}{r_{cornea}} - \frac{1}{r_{cornea} + t_{cornea}} \right) + \frac{3}{4\pi k_{lens}} \left( \frac{1}{r_{cornea} + t_{cornea}} - \frac{1}{r_{cornea} + t_{cornea} + t_{lens}} \right)$$

By inserting typical values to the above equations and choosing water as an exemplary cooling medium fluid, the mass flow rate can be calculated as 8.4 mg/sec when the temperature of the cooling medium fluid is set to be 1° C. It should be noted, however, that the mass flow rate of 8.4 mg/sec can differ for water at a different temperature to deliver the same amount of cooling power. For example, water at a temperature larger than 1° C. requires a mass flow rate larger than 8.4 mg/sec to deliver the same amount of cooling power.

From this calculation, the temperature of the fluid ($T_{fluid}$) should be 0~15° C. and the mass flow rate ($m_{fluid}$) at the nozzle outlet should be 5~50 mg/sec to cool the cornea for reduction of chronic pain. It should be noted, however, that initial cooling requires a larger cooling power than that of steady cooling to rapidly cool the cornea, and therefore requires a larger fluid mass flow rate. For example, in some embodiments, the mass flow rate at the nozzle outlet that can cool the cornea down to 12° C. in 5 seconds can be 5~500 mg/sec.

In some embodiments, the chilled air cooled by the cooling device 1300 can make the temperature of the fluid ($T_{fluid}$) lower than the freezing point of the fluid. For such case, latent heat of the fluid can increase the rate of cooling of the fluid.

Equation 1 can further be simplified by using typical thermal properties of cornea and lens and thereby using $R_{tot}=6.5$ K/W. With $R_{tot}=6.5$ K/W, $T_{lens}$ is calculated to be 10° C. Additionally, the variables $q_{cooling}=h_{cornea}(37-T_{cornea})=0.31$ W for $T_{cornea}=12°$ C. can be set, resulting in Equation 3:

$$0.31 = m_{fluid} c_{fluid}(10 - T_{fluid})$$ (Equation 3)

If the cooling temperature at the outer surface of cornea is set at lower than 12° C. for effective control of chronic pain (i.e., $T_{corena}$ is set at lower than 12° C. for effective analgesia), then the minimum cooling power of the fluid ($P_{fluid}$) should be accordingly to Equation 4:

$$P_{fluid} = m_{fluid} c_{fluid}(10 - T_{fluid}) \geq 0.3 \text{ W}$$ (Equation 4)

In some embodiments, the total cooling power of Peltier modules or other types of cooling element to deliver $P_{fluid} \geq 0.3$ W is greater than 0.3 W.

The minimum initial cooling power to cool cornea from its normal temperature (e.g., 33° C.) to the anesthesia temperature (12° C.) in tinitial can be calculated by:

$$P_{fluid,initial} = m_{cornea,lens} c_{cornea,lens}(33-12)/t_{initial} \geq 3W$$ (Equation 5)

where $m_{cornea,lens}$ and $c_{corena,lens}$ are the total mass of cornea and the bandage lens and effective heat capacity of cornea and the bandage lens, respectively. For example, the minimum initial cooling power of the fluid ($P_{fluid,initia}$) should be larger than 3 W (Equation 5), when $m_{cornea,lens}$ and $c_{cornea,lens}$ are 0.1 g and 3 J/g-K, respectively. In some embodiments, the total cooling power of Peltier modules or other types of the cooling element to deliver $P_{fluid} \geq 3$ W is between 3 W and 100 W. Accordingly, the initial mass flow rate of the fluid should be 93 mg/sec when the temperature of the cooling medium fluid and $t_{initial}$ are set to be 1° C. and 5 seconds, respectively. It should be noted that the cooling medium fluid at a temperature larger than 1° C. or $t_{initial}$ smaller than 5 seconds requires the initial mass flow rate larger than 93 mg /$_{sec}$. From this calculation, in some embodiments, the temperature of the fluid ($T_{fluid}$) is between 0~15° C. and the mass flow rate ($m_{fluid}$) at the nozzle outlet is 5~500 mg/sec to cool the cornea down to 12° C. in 5 seconds for reduction of chronic pain during the initial cooling period. In some embodiments, the initial mass flow rate can be 5~500 mg/sec.

In some embodiments, the cooling devices described herein can continuously deliver mist to the eye for a set period of time (e.g., for 1-2 hours). In other embodiments, the cooling devices described herein can be configured to deliver fluid automatically at set times (e.g., to deliver fluid for 15-60 seconds every 1-60 minutes). In other embodiments, the cooling devices described herein can be completely manually operated.

Advantageously, the devices described here can provide chilled fluid directly to the surface of the eye to cool and anesthetize the cornea thereunder (i.e., anesthetize the entire cornea at all depths). By applying the fluid (e.g., in mist, liquid, or a mixture of cold gas and ice particles form) to the surface of the eye, the tissue of the cornea can be cooled enough to be anesthetized without touching the eye with a solid device that would be painful or irritating to the eye, e.g., after PRK surgery or IVT. Additionally, the devices described herein can advantageously anesthetize the tissue without the use of pharmacological anesthetics, of which a prolonged use can slow down cornea or sclera recovery or can cause irritation of eye.

In some embodiments, the devices described herein can be used to cool tissues other than the tissues of the eye. For example, the devices described herein can be used to control chronic pain associated with arthritis in finger and toe joints (e.g., Gout arthritis) or pain associated with burn wounds. In particular, the chilled mist can cool burn wounds with the minimum mechanical stimulus to sensitive tissues.

In some embodiments, the devices described herein can be used to optimize the therapeutic effects of a nebulizer by controlling the temperature of a medication liquid or mist droplets. For example, the particle sizes of medication mist droplets, the viscosity of the medication liquid, respiration rate, or the functions of medication protein can be optimized by controlling the temperature of the medication liquid, mist droplets, or both medication liquid and mist droplets.

In some embodiments, the devices described herein can be used to optimize the quality of spray coating on a target surface by controlling temperature of the coating fluid. For example, the coating liquid with a lower temperature can evaporate slowly, allow the coating liquid to evenly spread on a hydrophilic surface, and thereby increase the uniformity of the resultant coating on a hydrophilic surface. On the other hand, the coating liquid with a high temperature can evaporate rapidly, reduce the congregation of the coating liquid on a hydrophobic surface, and therefore increase the uniformity of resultant coating on a hydrophobic surface.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A hand-held or wearable device for cooling tissue of an eye of a patient, comprising:
   a reservoir having fluid therein;
   a support connected to the reservoir and configured to be positioned over a face of the patient;
   a nozzle connected to the support and fluidically connected to the reservoir, the nozzle configured to pass the fluid from the reservoir onto a surface of the eye;
   a fluid cooler configured to cool the fluid after the fluid is output from the reservoir and before the fluid exits the nozzle such that the fluid exits the nozzle at a temperature between −100° C. and 15° C.; and
   an ultrasonic vibrator coupled to the nozzle and configured to generate mist from at least part of the fluid,
   wherein the support is coupled to the nozzle such that the nozzle is aligned to a center of a cornea of the eye when the support is positioned over the face of the patient, and
   wherein the nozzle is off-axis with respect to a central axis of the cornea to allow for unobstructed sight while the nozzle is aligned to the cornea of the eye to allow the fluid to be ejected to the center of the cornea.

2. The device of claim 1, wherein the temperature is between −10° C. and 10° C.

3. The device of claim 1, wherein the temperature is between 0° C. and 15° C.

4. The device of claim 1, wherein a mass flow rate of the fluid as the fluid exits the nozzle is between 5 mg/sec and 500 mg/sec.

5. The device of claim 1, wherein a cooling power of the fluid is greater than or equal to 0.3 W.

6. The device of claim 1, wherein the fluid comprises a fluid particle that has a volume smaller than 1 mm$^3$.

7. The device of claim 1, further comprising a pump configured to pump the fluid from the reservoir to the nozzle.

8. The device of claim 1, wherein the fluid cooler comprises one or more Peltier modules.

9. The device of claim 8, wherein a total cooling power of the one or more Peltier modules is between 0.3 W and 100 W.

10. The device of claim 1, wherein the fluid cooler comprises a vapor compression chiller.

11. The device of claim 1, wherein the fluid cooler comprises a Joule-Thomson cooler.

12. The device of claim 1, wherein the fluid cooler comprises a Stirling cycle cooler.

13. The device of claim 1, wherein the fluid cooler comprises a passive cooler.

14. The device of claim 1, further comprising a temperature sensor configured to detect a temperature of the fluid at the nozzle.

15. The device of claim 14, further comprising a controller configured to regulate the fluid cooler based upon the detected temperature.

16. The device of claim 1, wherein the fluid does not include a pharmacological anesthetic.

17. The device of claim 1, further comprising a cone-shaped end piece coupled to the nozzle, the cone-shaped end piece configured to be positioned on tissue outside of the eye of the patient while maintaining the nozzle spaced away from the eye.

18. The device of claim 1, wherein the support is wearable so as to be worn by the patient.

* * * * *